United States Patent
Wu et al.

(10) Patent No.: US 11,419,826 B2
(45) Date of Patent: Aug. 23, 2022

(54) SURFACE-MODIFIED MESOPOROUS SILICA NANOPARTICLE FOR BLOOD-BRAIN BARRIER PENETRATION, TUMOR TARGETING AND CANCER METASTASIS TREATMENT, METHODS OF PRODUCTION AND USES THEREOF

(71) Applicant: NANO TARGETING & THERAPY BIOPHARMA INC., Taipei (TW)

(72) Inventors: Cheng-Hsun Wu, New Taipei (TW); Yi-Ping Chen, Keelung (TW); Si-Han Wu, Taichung (TW); Chung-Yuan Mou, Taipei (TW)

(73) Assignee: NANO TARGETING & THERAPY BIOPHARMA INC., Taipei (TW)

( * ) Notice: Subject to any disclaimer, the term of this patent is extended or adjusted under 35 U.S.C. 154(b) by 119 days.

(21) Appl. No.: 16/864,017

(22) Filed: Apr. 30, 2020

(65) Prior Publication Data

US 2020/0345649 A1 Nov. 5, 2020

Related U.S. Application Data

(60) Provisional application No. 62/843,033, filed on May 3, 2019.

(51) Int. Cl.
| | |
|---|---|
| *A61K 9/51* | (2006.01) |
| *A61K 47/60* | (2017.01) |
| *A61K 41/00* | (2020.01) |
| *A61K 45/06* | (2006.01) |
| *B82Y 5/00* | (2011.01) |

(52) U.S. Cl.
CPC .......... *A61K 9/5115* (2013.01); *A61K 9/5146* (2013.01); *A61K 9/5169* (2013.01); *A61K 9/5192* (2013.01); *A61K 41/0052* (2013.01); *A61K 47/60* (2017.08); *A61K 45/06* (2013.01); *B82Y 5/00* (2013.01)

(58) Field of Classification Search
CPC .. A61K 9/5115; A61K 9/5146; A61K 9/5156; A61K 9/5192; A61K 9/0019; A61K 9/0085; A61K 31/1704; A61K 41/0052; A61K 45/06; A61K 47/60; A61K 35/00; A61P 25/00; A61P 25/16; A61P 25/28; B82Y 5/00
See application file for complete search history.

(56) References Cited

PUBLICATIONS

Morry et al., Targeted Treatment of Metastatic Breast Cancer by PLK1 and siRNA Delivered by an Antioxidant Nanoparticle, AACR, pp. 763-773. (Year: 2017).*

(Continued)

*Primary Examiner* — Carlos A Azpuru
(74) *Attorney, Agent, or Firm* — Prosyla Group PC

(57) ABSTRACT

The present disclosure relates to mesoporous silica nanoparticles (MSNs) with specific modifications as drug delivery systems containing both tumor targeting and blood-brain barrier (BBB) penetration properties suitable for cancer treatment and/or CNS disease treatment. The present disclosure also relates to method of preparing MSNs and the MSNs prepared by the method as described herein.

23 Claims, 8 Drawing Sheets
(2 of 8 Drawing Sheet(s) Filed in Color)

(56) References Cited

PUBLICATIONS

B.I. Tamba et al., "Tailored surface silica nanoparticles for blood-brain barrier penetration: Preparation and in vivo investigation," Arabian Journal of Chemistry (2018) 11, pp. 981-990.

Chen, Yijie et al., "Highly effective inhibition of lung cancer growth and metastasis by systemic delivery of siRNA via multimodal mesoporous silica-based nanocarrier," Biomaterials, 2014, vol. 35, pp. 10058-10069.

Devi Wahyuningtyas, the Abstract of "Surface Modification of Upconversion Nanoparticles for Biological Usage," Master's Thesis, National Taiwan University of Science and Technology, Department of Chemical Engineering, 2015.

European Search Report (ESR) dated Feb. 24, 2021 issued in EP Application No. 109114658.

Gao, Yu et al., "The Architecture and Function of Monoclonal Antibody-Functionalized Mesoporous Silica Nanoparticles Loaded with Mifepristone: Repurposing Abortifacient for Cancer Metastatic Chemoprevention," www.small-journal.com, 2016, No. 19, pp. 2295-2608.

Morry, Jingga et al., "Targeted Treatment of Metastatic Breast Cancer by PLK1 siRNA Delivered by an Antioxidant Nanoparticle Platform," AACR, 2017, pp. 763-773.

Ngamcherdtrakul, Worapol et al., "Cationic Polymer Modified Mesoporous Silica Nanoparticles for Targeted siRNA Delivery to HER2+ Breast Cancer," Advanced Functional Materials, 2015, vol. 25, pp. 2646-2659.

Office Action dated Mar. 3, 2021 in Taiwan Application. No. 109114658.

Fing-Wei Wu, the Abstract of "Developing Functional Silica Nanohybrid Co-carrier for Synergistic Anticancer Therapy," Waster's Thesis, National Taiwan University, Department of Chemistry.

Townson, Jason L et al., "Re-examining the Size/Change Paradigm: Differing in Vivo Characteristics of Size- and Charge-Matched Mesoporous Silica Nanoparticles," JACS, 2013, vol. 135, pp. 16030-016033.

Townson, Jason L., Supporting Information: "Re-Examining the Size/Charge Paradigm: Differing In Vivo Characteristics of Size and Charge-Matched Mesoporous Silica Nanoparticles," 19 pages.

Zhang, Min and Jiang, Li, "Doxorubicin Hydrochloride-Loaded Mesoporous Silica Nanoparticles Inhibit Non-Small Cell Lung Cancer Metastasis by Suppressing VEGF-Mediated Angiogenesis," J Biomed Nanotech, vol. 12, 2016, pp. 1975-1986.

\* cited by examiner

200
SURFACE-MODIFIED MESOPOROUS SILICA NANOPARTICLE FOR BLOOD-BRAIN BARRIER PENETRATION, TUMOR TARGETING AND CANCER METASTASIS TREATMENT, METHODS OF PRODUCTION AND USES THEREOF

This application is a U.S. Non-Provisional Patent Application of Provisional Patent Application No. 62/843,033, filed May 3, 2019, the entirety of which is referenced herein.

FIELD OF THE INVENTION

The present invention relates to mesoporous silica nanoparticles as a drug delivery system capable of loading bioactive ingredients for treating cancer, or as an active agent for inhibiting cancer metastasis.

BACKGROUND OF THE INVENTION

Mesoporous silica nanoparticles (MSNs) have been deemed to have great potential as drug delivery systems due to their unique physical/chemical properties, such as large pore volume, chemical/thermal stability, high loading capacity, adjustable surface properties and excellent biocompatibility. In the past decade, MSNs are widely used in disease treatment because they can deliver various kinds of therapeutic drugs to the target site. Among the disease, cancer is the second leading cause of death globally, and is responsible for an estimated 9.6 million deaths in 2018. Nanoparticles have been successful to aim to cure multiple types of cancer and have demonstrated specific therapeutic effects based on the tumor-targeting and controlled/sustained drug release properties of nanoparticle. The passive tumor targeting of nanoparticle is based on enhanced permeability and retention (EPR) effect of solid tumors, the leaky vasculature and the lack effective lymphatic drainage in solid tumor that make nanoparticles accumulate in the tumor.

Another challenge is to treat diseases of central nervous system (CNS), which are large field of unmet medical needs such as Alzheimer's (AD), Parkinson's disease (PD) and brain tumors, owing to the blood-brain barrier (BBB) restrict most of therapeutic drugs transport into the brain. Essentially 100% of the macromolecular drugs and over 95% of the small-molecule drugs are unable to enter into brain. Versatile nanoparticle drug delivery systems are considered as a potential strategy to overcome the BBB restriction for central nervous system (CNS) disease treatment.

In addition, since the likelihood of patients suffered from a cancer would dramatically increase when cancer metastasis occurs, it is also crucial to prevent, inhibit or suppress the occurrence of cancer metastasis so that the patients having cancers, in particular metastatic cancers, can have good prognosis.

Hence, there is still needs for improved mesoporous silica nanoparticles as drug delivery systems or active ingredients and a reliable way to synthesize such mesoporous silica nanoparticles.

SUMMARY OF THE INVENTION

The present disclosure relates to mesoporous silica nanoparticles (MSNs) with specific modifications suitable as drug delivery systems containing both tumor targeting and blood-brain barrier (BBB) penetration properties suitable for cancer treatment and/or CNS disease treatment.

The present disclosure also relates to mesoporous silica nanoparticles (MSNs) with specific modifications suitable as a therapeutic agent for preventing, inhibiting or suppressing cancer metastasis.

The present disclosure also provides the products prepared by the method as described above.

BRIEF DESCRIPTIONS OF THE DRAWINGS

The subject patent or application file contains at least one drawing executed in color. Copies of this patent or patent application publication with color drawing(s) will be provided by the Office upon request and payment of the necessary fee.

FIG. 1 shows the TEM images of 30 nm MSN-PEG (FIG. 1A) and MSN-PEG+TA (2:1) (FIG. 1B).

FIG. 2 shows the ratio of particle accumulation in tumor to liver (tumor/liver) for 30 nm MSN-PEG FIG. 3 shows the ratio of particle accumulation in tumor to liver (tumor/liver) for 30 nm MSN-PEG+TA nanoparticles FIG. 4 shows 3D images of 30 nm MSN-PEG+TA (FIG. 4A) and 30 nm MSN-PEG+THPMP (FIG. 4B) in brain vessel were detected by two-photon fluorescence microscopy.

DETAILED DESCRIPTION OF THE INVENTION

Figure 1A:
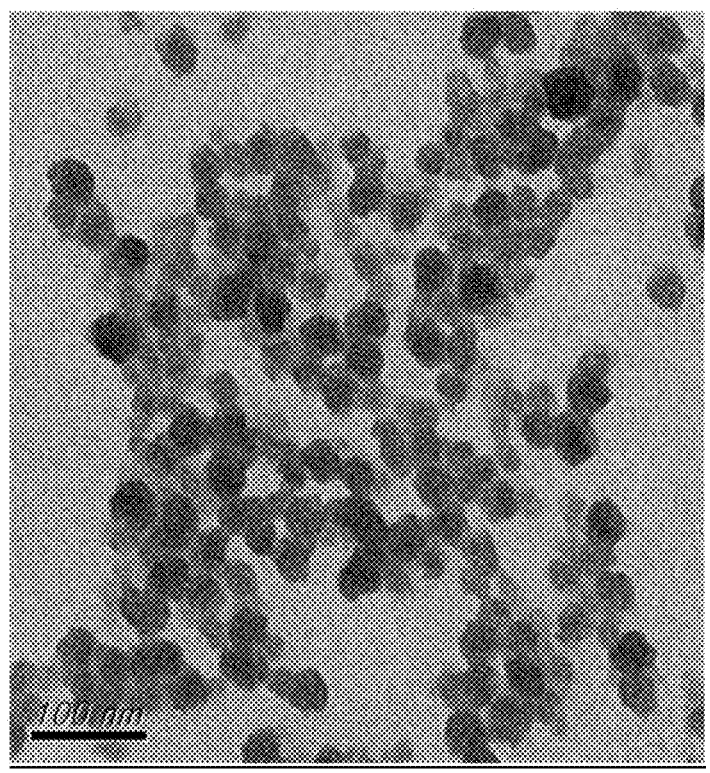

In order to facilitate the understanding of the disclosure herein, terms as used herein are hereby defined below.

In the context of the specification and the claims, the singular forms "a", "an" and "the" include plural referents, unless specifically indicated otherwise. Unless otherwise stated, any and all examples or exemplary language (e.g., "such as") provided herein are merely used for better illustration of the present invention, instead of limiting the scope of the present invention.

It is to be understood that any numerical range recited in this specification is intended to include all sub-ranges encompassed therein. For example, a range from "50 to 70° C." includes all sub-ranges and specific values between the stated minimum value of 50° C. and the stated maximum value of 70° C., inclusive, e.g. from 58° C. to 67° C., and from 53° C. to 62° C., 60° C. or 68° C. Since the numerical ranges disclosed are continuous, they contain each numerical value between the minimum and maximum value. Unless otherwise specified, the various numerical ranges indicated in this specification are approximate.

In the present invention, the term "about" refers to an acceptable deviation of a given value measured by a person of ordinary skill in the art, depending, in part, on how to measure or determine the value.

In the present invention, unless particularly specified, the prefix "nano-" as used herein means a size of about 300 nm or less. Unless particularly specified, the prefix "meso-" as used herein, unlike the definition suggested by IUPAC, means a size of about 5 nm or less.

In the present invention, the term "silane" as used herein refers to derivatives of SiH$_4$. Normally, at least one of the four hydrogens is replaced with substituents such as alkyl, alkoxyl, amino, etc. as described below. The term "alkoxysilane" as used herein refers to a silane having at least one alkoxyl substituent directly bonded to the silicon atom. The term "organo-alkoxysilane" as used herein refers to a silane having at least one alkoxyl substituent and at least one hydrocarbyl substituent directly bonded to the silicon atom. The term "silicate source" as used herein refers to substances which can be deemed as a salt form or an ester form of orthosilicic acid, for example sodium orthosilicate, sodium metasilicate, tetraethyl orthosilicate (tetraethoxysilane, TEOS), tetramethylorthosilicate, tetrapropylorthosilicate. Optionally, the hydrocarbyl substituent can be further substituted or interrupted with a heteroatom.

In the present invention, the term "hydrocarbyl" as used herein refers to a mono-valent radical derived from hydrocarbons. The term "hydrocarbon" as used herein refers to a molecule that consists of carbon and hydrogen atoms only. Examples of the hydrocarbons include, but are not limited to, (cyclo)alkanes, (cyclo)alkenes, alkadienes, aromatics, etc. When the hydrocarbyl is further substituted as mentioned above, the substituent can be halogens, amino groups, a hydroxy group, a thiol group, etc. When the hydrocarbyl is interrupted with a heteroatom as mentioned above, the heteroatom can be S, O or N. In the present invention, a hydrocarbyl preferably comprises 1 to 30 C atoms.

In the present invention, the term "alkyl" refers to a saturated, straight or branched alkyl, which comprises preferably 1-30 carbon atoms, and more preferably 1-20 carbon atoms. Examples of alkyl include, but are not limited to, methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, iso-heptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl or the like.

In the present invention, the term "alkylene" refers to a divalent radical of an alkyl as noted above. The term "short chain" represents that the radical or repeating unit contains at most 6 carbon atoms in the main chain, preferably at most 4 carbon atoms.

In the present invention, the term "alkoxyl" or "alkoxy" as used herein means a group having a formula "—O-alkyl," wherein the definition of the "alkyl" in said formula has the meaning of "alkyl" as stated above.

In the present invention, the term "cycloalkyl" as used herein means a saturated or partially unsaturated cyclic carbon radical containing 3 to 10 ring carbon atoms and more preferably 3 to 8 ring carbon atoms, and optionally an alkyl substituent(s) on the ring. Examples of cycloalkyl include, but are not limited to, cyclopropyl, cyclopropenyl, cyclobutyl, cyclopentyl, cyclohexyl, 2-cyclohexen-1-yl, and the like.

In the present invention, the term "halogen" or "halo" denotes fluorine, chlorine, bromine or iodine.

In the present invention, the term "amino" as used herein means a functional group of the formula —NR$_1$R$_2$, wherein R$_1$ and R$_2$ each independently represent hydrogen or a hydrocarbyl group as defined above.

In the present invention, the term "aqueous phase" as used herein means a phase substantively miscible with water. Examples of the aqueous phase include, but are not limited to, water per se, aqueous buffers, aqueous dimethylsulfoxide (DMSO) solutions, aqueous alkanolic solutions, etc. The aqueous phase may be adjusted to be acidic, neutral or alkaline, based on the demand of the synthesis and/or the stability of the substance present in the aqueous phase.

In the present invention, the term "oil phase" as used herein means a phase substantively immiscible with the aqueous phase as mentioned above. Examples of the oil phase include, but are not limited to, liquid, substituted or unsubstituted (cyclo)alkanes, such as hexane, decane, octane, dodecane, cyclohexane, etc.; substituted or unsubstituted aromatic solvents, such as benzene, toluene, xylene, etc.

In the present invention, the term "bioactive ingredient" as used herein refers to substance having an activity in an organism. Examples of the bioactive ingredient include, but are not limited to, a small molecule drug, a protein such as an enzyme and a protein drug, an antibody, a vaccine, an antibiotic or a nucleotide drug.

In the present invention, the term "solid silica nanoparticle" as used herein refers to a silica nanoparticle having no porous structure on its surface, in particular no mesopore(s).

The invention surprisingly found that in vitro and in vivo actions of the MSNs may be regulated by the surface modifications and physicochemical properties of MSNs including size, shape, surface charge, and spatial distribution of functional moieties as determinants of tumor targeting ability (e.g., EPR effect) and BBB penetration properties of MSNs. MSNs modified with short-chain poly(alkylene glycol)(PAG), e.g., poly(ethylene glycol) (PEG), poly(propylene glycol) (PPG), PEG-PPG copolymers, etc., on the exterior surface and also introduced charge molecules hidden within PAG layer in a specific PAG/charge molecules mole ratio. Those modifications, spatial arrangement, and charge cause MSNs reveal characterizations including minimal non-specific binding, proper circulation time in physiological environment and transport from blood to brain.

Poly(alkylene glycol) (PAG), e.g., poly(ethylene glycol) (PEG), poly(propylene glycol) (PPG), etc., modification can prevent MSN from adsorbing serum proteins and reduce the clearance by the reticuloendothelial system. Further modifying agent(s) can be introduced to modify the properties of MSNs (e.g., surface properties, etc.). PEG is used as a surface modifying agent and it is observed that if the modifying agents are exposed to the exterior surface rather than hidden deep in the PEG layer, the MSN will exhibit non-specific binding to proteins or cells in the physiological environment and result in rapid clearance in vivo and less accumulation of MSN in tumor.

Accordingly, the present disclosure uses charge modulating molecules, in particular agents with positively charged group, with the length shorter than the PEG on the surface of MSN. To evaluate the effect of surface charge on EPR effect of PEGylated MSN (MSN-PEG), the present disclosure synthesizes size-, shape-, hydrodynamic diameter-, and spatial distribution-matched MSNs which have various surface charge through modulating the ratio of PEG to charge molecules present on MSN-PEG. Biodistribution of MSNs in tumor-bearing mice studies reveal that one of the factors affecting the efficacy of administration and recirculation of MSNs is the zeta potential. For instance, the zeta potential (in pH 7.4 condition) of the modified MSNs may range from −22 to +25 mV, preferably −22 to +21 mV, −21 to +25 mV, etc. In one embodiment, 30 nm MSN-PEG+TA (MSN modified with PEG and N-[3-(trimethoxysilyl)propyl]-N,N,N-trimethylammonium chloride (TA)) has a zeta potential ranging from −22 to +21 mV, preferably ranging from about −15 to +17 mV, more preferably ranging from about −13 to +7 mV, or in another instance up to +4 mV, and it will show an excellent EPR effect (e.g., the ratio of tumor signal to liver signal (tumor/liver) is higher than 1 and the tumor/liver value is also higher than the tumor/liver value of MSN-PEG). In one embodiment, 50 nm MSN-PEG+TA has a zeta potential (in pH 7.4 condition) ranging from −21 to +25 mV, preferably ranging from about −21 to +18 mV, and it will show an excellent EPR effect.

Another factor affecting the tumor targeting ability (EPR effect) of the surface modified MSNs is the molar ratio of PEG groups to positively charged groups (PEG/positively charged group) on MSN, wherein the PEG/(positively charged group) molar ratio is determined by elemental analysis. The PEG/positively charged group ratio may fall within a specific range. In one instance, the ratio ranges from 0.5 to 15, preferably from about 2 to 10 and more preferably 2 to 6.5. It is observed and expected that MSNs with such a specific PEG/charged group ratio could show an excellent EPR effect.

Other factors affecting the efficacy of MSNs acting as a drug delivery system may include, but are not limited to, particle size, types of the (surface) modifying agents, morphology of the particles, etc.

The inventors also surprisingly found that the surface modified MSNs are able to cross blood-brain barrier (BBB). The BBB is a vital physiological barrier in the central nervous system that regulates the movement of ion and molecule from circulating blood into brain and protects the brain from invading pathogens and toxic agent. However, the BBB is also a challenging for treating brain disease, most of drugs are hindered by BBB. The prior method for overcoming the BBB are still limited, versatile nanoparticles with smaller size, and functionalized surface is consideration for crossing BBB, however the effect of these diverse characterizations of nanoparticle on regulating BBB penetration remains unclear. In order to develop the unique silica nanoparticle with BBB penetration ability for drug delivery in CNS disease, the present disclosure is directed to compositions and methods that synthesizes different sizes, charges, and functional ligands of MSN in a rational design.

The present disclosure thus demonstrates that MSN-PEG+TA with a specific range of surface charge have the ability to cross the BBB. In one embodiment, 30 nm MSN-PEG+TA with a zeta potential ranging from −15 to +21, preferably ranging from about −13 to +17 mV, more preferably ranging from about −13 to +7 mV (in one instance, 6.4 mV) in pH 7.4 condition would have the ability to cross the BBB. As noted above, the surface charge of MSNs can be modulated by conjugating different ratio of PEG/charge molecule to MSN and the charge molecule must be presented within the PEG layer. The molar ratio of PEG group to positively charged group (PEG/positively charged group) on of MSN, the PEG/(positively charged group) mole ratio is determined by elemental analysis. The PEG/positively charged group ratio may fall within a specific range. In one instance, said ratio ranges from about 0.5 to about 15, preferably from about 2 to about 10 and more preferably from about 2 to about 6.5 (in one instance, 6.13). It is observed and expected that MSNs with such a specific PEG/charged group ratio could show an excellent BBB penetration.

MSN containing both EPR effect and BBB penetration capability will show advantages to being a high potential drug delivery system for brain associated cancers and CNS disease treatment. The all examples, the ingredients, the reaction conditions or parameters illustrated in the examples are merely for illustration purposes and are not intended to limit the material or the preparation method by the exemplary embodiments described herein.

Surface-Modified Mesoporous Silica Nanoparticles (MSNs) and Method of Preparing the Same In one aspect, the present disclosure provides a mesoporous silica nanoparticle, comprising organic modification on the surface thereof, having a zeta potential within the range from about −22 mV to about +25 mV at pH 7.4 and a particle size of about 50 nm or less, wherein the organic modification comprises poly(ethylene glycol) moiety and at least one positively charged group-containing oligomer/polymer moiety. The molar ratio of poly(ethylene glycol) moiety to positively charged group-containing oligomer/polymer moiety may fall within a specific range, e.g., from about 0.5 to about 15, which can be determined by elemental analysis.

In one embodiment, the mesoporous silica nanoparticle of the present disclosure has a particle size of about 30 nm or less.

In one embodiment, the mesoporous silica nanoparticle of the present disclosure has a zeta potential within the range from about −15 mV to about +4 mV at pH 7.4; in another preferred embodiment the zeta potential ranges from about −13 to about +7 mV at pH 7.4.

In one embodiment, the mesoporous silica nanoparticle of the present disclosure has a ratio of poly(ethylene glycol) moiety to positively charged group-containing oligomer/polymer moiety within a specific range from about 2 to about 6.5.

In one embodiment, the surface modification of MSNs comprises organic modification, including at least one moiety for enhancing the bioavailability and at least one moiety for adjusting the characteristic of surface charge. In one embodiment, the moiety for enhancing the bioavailability is derived from or introduced by a surface modifying agent. In one embodiment, the moiety for adjusting the characteristic of surface charge is derived from a charged modulating molecule, in particular positively charged group containing oligomer/polymer. In one embodiment, the positively charged group containing oligomer/polymer may be nitrogen-containing oligomer/polymer.

In one embodiment, the organic modification is derived from or selected from poly(alkoxylene glycol) (PAG) such as poly(ethylene glycol) (PEG), poly(propylene glycol) (PPG), PEG-PPG copolymers, etc.; polyethylenimine (PEI); alkoxylsilane-terminated (poly)alkylene(poly)amine, such as N-[3-(trimethoxysilyl)propyl]-N,N,N-trimethylammonium chloride (TA), N-[3-(Trimethoxysilyl)propyl]ethylenediamine (EDPT), $N^1$-(3-Trimethoxysilylpropyl)diethylenetriamine, etc.; organo-alkoxysilane such as 3-aminopropyltrimethoxysilane (APTMS), propyl triethoxysilane, butyl trimethoxysilane, octyltrimethoxysilane, diphenyl diethoxysilane, n-octyltriethoxysilane, mercapto propyl trimethoxysilane, chloro methyl trimethoxysilane, isobutyl triethoxysilane, 3-aminopropyl triethoxysilane, ethyl trimethoxy styrene silane, methyl triethoxysilane, phenyltriethoxysilane (PTEOS), phenyltrimethoxysilane (PTMOS), methyltrimethoxysilane (MTMOS), ethyltriacetoxysilane (ETAS), N-(trimethoxysilylpropyl)ethylenediaminetriacetic acid (EDTAS), (3-trihydroxysilyl) propyl methylphosphonate (THPMP), methyltriacetoxysilane(MTAS), (3-mercaptopropyl) trimethoxysilane (MPTMS), zwitterionic silane.

In one embodiment, the bioactive ingredient is loaded onto the nanoparticles. In another embodiment, bioactive ingredient is loaded into the nanoparticles. In yet another embodiment, bioactive ingredient is loaded onto and also loaded into the nanoparticles.

Mesoporous silica nanoparticles (MSNs) possess well-defined structure and high density of surface silanol groups which can be modified with a wide range of organic functional groups. The different sizes of MSNs are prepared using an ammonia base-catalyzed method. The particle size is controlled by adjusting ammonia concentration, amount and concentration of the silane source, and reaction temperature, etc.

In one aspect, MSNs can be prepared with the following steps: (a) providing an alkaline solution containing a surfactant at a concentration sufficient for forming micelles; (b) introducing silane source(s) into the solution; (c) introducing surface modifying agents comprising at least one PEG-modified silane and at least one positively charged group containing silane into the solution; (d) conducting hydrothermal treatment to the solution; (e) collecting the products; (f) removing the residual surfactant(s) from the products; and optionally (g) purifying or cleaning the products.

Typically, 0.29 g of CTAB was dissolved in 150 mL of ammonium hydroxide solution (0.1-0.2M) at the desired temperature (50-60° C.) in a sealed beaker. After 15-minutes of stirring, the sealed membrane was removed, and then 2.5 mL of ethanolic RITC-conjugated APTMS and 2-2.5 mL of ethanolic TEOS (0.8-0.9M) were added to the solution under vigorous stirring (600 rpm). After 1 hour of stirring, the 550 µL of PEG-silane (2-[methoxy(polyethyleneoxy)propyl]-trimethoxysilane) with different molar ratio of PEG-silane to TA-silane (N-[3-(trimethoxysilyl)propyl]-N,N,N-trimethyl-ammonium chloride) (the ratio of PEG/TA=15:1, 10:1, 7:1, 3:1, 2:1, 1:2; the amount of TA-silane is 0.04-1.2 mL) in 2 mL of ethanol were introduced into the reaction. After the mixture was stirred for 30 minutes, the mixture was aged at desired temperature (50-60° C.) without stirring for at least 12 hours. And then the solution was sealed and placed in an oven at 70° C. for 24 hours of hydrothermal treatment. The as-synthesized sample was washed and collected by centrifugation or cross-flow system. For removing the surfactant in the pores of the MSNs, the as-synthesized sample was incubated in 40 mL of acidic ethanol containing 678 µL (first time) and 40 µL (second time) of hydrochloric acid (37%) for 1 hour of extraction respectively at 60° C. The products were washed and harvested by centrifugation or cross-flow system and finally stored in 90% ethanol. For different functional group modified MSN-PEG synthesis, replace the TA-silane with PEI-silane, EDPTMSN-silane or other functional-silanes.

In one embodiment, the silane source comprises tetraethoxysilane (TEOS), tetramethoxysilane (TMOS), sodium silicate or a mixture thereof. In one embodiment, the surface modifying agent is 2-[methoxy(polyethyleneoxy)propyl]-trimethoxysilane (PEG-trimethoxysilane), 3-aminopropyltrimethoxysilane (APTMS), propyl triethoxysilane, butyl trimethoxysilane, octyltrimethoxysilane, diphenyl diethoxysilane, n-octyltriethoxysilane, mercapto propyl trimethoxysilane, chloro methyl trimethoxysilane, isobutyl triethoxysilane, 3-aminopropyl triethoxysilane, ethyl trimethoxy styrene silane, methyl triethoxysilane, phenyltriethoxysilane (PTEOS), phenyltrimethoxysilane (PTMOS), methyltrimethoxysilane (MTMOS), ethyltriacetoxysilane (ETAS), N-(trimethoxysilylpropyl)ethylenediaminetriacetic acid (EDTAS), (3-trihydroxysilyl)propyl methylphosphonate (THPMP), methyltriacetoxysilane(MTAS), N-[3-(trimethoxysilyl)propyl]ethylenediamine, trimethoxysilylpropyl (polyethlenimine), N-trimethoxysilylpropyl-N,N,N-trimethylammonium chloride, (3-mercatopropyl) trimethoxysilane (MPTMS), zwitterionic silane or a mixture thereof.

Examples of surfactants suitable for preparing MSNs include, but are not limited to, cationic surfactants, anionic surfactants and non-ionic surfactants. Proper surfactants are selected based on the conditions of reaction, such as pH value, ionic strength, temperature, reactants and products, etc. Examples of cationic surfactants include, but are not limited to, pH-dependent primary, secondary, or tertiary amines with a long-chain hydrocarbyl group, and the terminal amine group bears positive charge when presenting below a specific pH value, such as primary and secondary amines become positively charged at pH<10, for example octenidine dihydrochloride; and permanently charged quaternary ammonium salts, e.g., cetrimonium bromide (CTAB), cetylpyridinium chloride (CPC), benzalkonium chloride (BAC), benzethonium chloride (BZT), dimethyldioctadecylammonium chloride, and dioctadecyldimethylammonium bromide (DODAB). Examples of anionic surfactants include, but are not limited to, sulfate, sulfonate, and phosphate salts or esters; such as ammonium lauryl sulfate, sodium lauryl sulfate (sodium dodecyl sulfate, SLS, or SDS), and the related alkyl-ether sulfates sodium laureth sulfate (sodium lauryl ether sulfate or SLES), and sodium myreth sulfate, docusate (dioctyl sodium sulfosuccinate), perfluorooctanesulfonate (PFOS), perfluorobutanesulfonate, alkyl-aryl ether phosphates, alkyl ether phosphates, etc. Examples of non-ionic surfactants include, but are not limited to, poly(oxyethylene)nonylphenyl ether, polyoxyethylene glycol sorbitan alkyl ester, polyethylene glycol alkyl ether, glucoside alkyl ether, polyethylene glycol octylphenyl ether, polyethylene glycol alkylphenyl ether, glycerol alkyl ester, polypropylene glycol alkyl ethers, block copolymers, poloxamers, cocamide MEA, cocamide DEA, lauryldimethylamine oxide or polyethoxylated tallow amine.

Size of MSNs

The different sizes of MSNs may prepared by using an ammonia base-catalyzed method. In one aspect, the MSNs are prepared under highly dilute and low surfactant conditions. In the present disclosure, MSNs have a diameter ranging from 20 to 200 nm, preferably 20 to 80 nm, more preferably 20 to 50 nm and even more preferably 30 to 40 nm. Control of the size of MSNs can be achieved by adjusting the ammonia concentration, amount and concentration of alkoxylsilane, reaction temperature, etc. Without being bound to the theory, when the ammonia concentration is higher, the size of MSNs may become larger and vice versa; when the amount of alkoxylsilane is larger, the of MSNs may become larger and vice versa; In various embodiments, 0.14-0.5 g CTAB in 150 mL ammonium hydroxide solution, the ammonia concentration ranges from 0.05 to 1.5M, preferably from 0.1 to 0.5M, more preferably from 0.1 to 0.256M; the amount of alkoxysilane added into 150 mL ammonium hydroxide solution ranges from 1 mL to 5 mL, preferably from 1 mL to 3 mL, more preferably from 2 mL to 2.5 mL of ethanolic TEOS (about 0.862M); and the reaction temperature ranges from 30° C. to 60° C., preferably from 40° C. to 60° C., more preferably from 50° C. to 60° C.; any combination of these conditions may serve as an embodiment of the present disclosure.

Surface Modification of MSNs

MSNs possess well-defined structure and high density of surface silanol groups which can be modified with a wide range of organic functional groups. Examples of functional groups include, but are not limited to, poly(alkoxylene glycol) (PAG) such as poly(ethylene glycol) (PEG), poly (propylene glycol) (PPG), PEG-PPG copolymers, etc.; polyethylenimine (PEI); alkoxylsilane-terminated (poly)alkylene(poly)amine, such as N-[3-(trimethoxysilyl)propyl]-N,N,N-trimethylammonium chloride (TA), N-[3-(Trimethoxysilyl)propyl]ethylenediamine (EDPT), $N^1$-(3-Trimethoxysilylpropyl)diethylenetriamine, etc.; organo-alkoxysilane such as 3-aminopropyltrimethoxysilane (APTMS), propyl triethoxysilane, butyl trimethoxysilane, octyltrimethoxysilane, diphenyl diethoxysilane, n-octyltriethoxysilane, mercapto propyl trimethoxysilane, chloro methyl trimethoxysilane, isobutyl triethoxysilane, 3-aminopropyl triethoxysilane, ethyl trimethoxy styrene silane, methyl triethoxysilane, phenyltriethoxysilane (PTEOS), phenyltrimethoxysilane (PTMOS), methyltrimethoxysilane (MTMOS), ethyltriacetoxysilane (ETAS), N-(trimethoxysilylpropyl)ethylenediaminetriacetic acid (EDTAS), (3-trihydroxysilyl)propyl methylphosphonate (THPMP), methyltriacetoxysilane(MTAS), (3-mercatopropyl)trimethoxysilane (MPTMS), zwitterionic silane.

Particularly important parameters of nanoparticle for bio-applications are particle size and surface properties, which would be expected to play key roles on the circulation half-life, pharmacokinetics, and bio-distribution of the nanoparticle. The size of MSNs affects the pharmacokinetics and bio-distribution thereof in body. MSNs having an ultra-small size (e.g., diameter <8 nm) would be usually quickly cleared by renal filtration, while larger nanoparticles (e.g., diameter >150 nm) are presented in the liver or spleen. Nanoparticles having a diameter within, e.g., 20-100 nm, generally exhibit a longer half-life in blood, which increases the propensity of extravasation of nanoparticle through fenestrations in tumor vasculature. Furthermore, nanoparticle with a small size (e.g., <50 nm) and a long circulation period in body may increase the capability of crossing the BBB. The surface of MSNs modified with functional groups will also change the properties and thereby bio-application performance of MSN. For example, poly(alkoxylene glycol) (PAG)-type group modification can make the particle exhibit better suspension in a medium, lower immunogenicity and longer circulation period in body. While MSNs without any surface modification normally bear negative charges on the surface, PEI, alkoxylsilane-terminated (poly)alkylene(poly)amine or amine-containing organo-alkoxysilane modification can make particle to have a positive or weak negative surface charge or to be electrically neutral on the surface. Carboxyl, phosphoryl, sulfonate-containing organo-alkoxysilane modifications can make particle to have strongly negative charges. In addition, combinations of functional groups on the surface of particles will provide multiple surface properties. Therefore, size and surface properties of particles can be designed or optimized based on the purpose in bio-applications.

Bioactive Ingredient

For the treatment of disease, at least one bioactive ingredient can be loaded onto and/or into MSNs, for example distributed within the space in MSNs, on the surface of MSNs, etc. The bioactive ingredient can be properly selected based on the size thereof and the concerned disorders/diseases. Examples of the bioactive ingredient include, but are not limited to, everolimus, trabectedin, abraxane, TLK 286, AV-299, DN-I01, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trapantibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR1 KRX-0402, lucanthone, LY317615, neuradiab, vitespan, Rta 744, Sdx 102, talampanel, atrasentan, Xr 311, romidepsin, ADS-I00380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1-H-pyrrolo[2,3-d]pyrimidin-5-yl)ethyl]benzoyl]-disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258, 3-[5-(methylsulfonylpiperadinemethyl)-indolyl]-quinolone, vatalanib, AG-013736, AVE-0005, goserelin acetate, leuprolide acetate, triptorelinpamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanibcanertinib, ABX-EGF antibody, erbitux, EKB-569, PKI-166, GW-572016, Ionafarnib, BMS-214662, tipifamib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, etc., fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracilmustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukindiftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)rapamycin, temsirolimus, AP-23573, RAD001, ABT-578, BC-210, LY294002, LY292223, LY292696, LY293684, LY293646, wortmarmin, ZM336372, L-779,450, PEG-filgrastim, darbepoetin, erythropoietin, granulocytecolony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-Asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab-tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa.

EPR Effect

In general, EPR-mediated passive targeting highly relies on the prolonged circulation time of nanocarriers. The enhanced permeability and retention (EPR) effect based tumor targeting would be approached by (1) high-density PEGylation; (2) spatial control of functional groups on the surface; (3) making of small mesoporous silica nanoparticles (MSN) and (4) controlling the protein corona formation. Particularly important two parameters are particle size and surface properties, which would be expected to play key roles on the circulation half-life, pharmacokinetics, and bio-distribution of the nanocarriers. Typically, the injected materials would be recognized and bound rapidly by serum opsonins, followed by phagocytosis and substantially accumulated in both the liver and the spleen (also known as the mononuclear phagocyte system). In addition, comprehensive studies highlighted protein corona neutrality as an important design in the development of targeted nanomaterial delivery and demonstrated that even a small difference in the surface heterogeneity could have chances to result in profoundly different interactions with cells and tissues. Therefore, the control and understanding of protein corona composition might be critical for developing successful EPR-targeted nanomedicines BBB Penetration Effect Blood-brain barrier (BBB) restricts most of therapeutic drugs transported into the brain. Nanomedicine can modulate the nanoparticle size, shape, surface charge, conjugated ligands to increase penetration of BBB. Nanoparticle conjugated with targeting ligands that bind to receptors on endothelial cells, such as transferrin, lactoferrin, glutathione and low-density lipoprotein receptors, may also promote BBB penetration. However, modification with targeting ligands on nanoparticle exterior surface may also affect the suspension and circulation of nanoparticles in blood and accelerate the blood clearance of nanoparticles. The present invention increases the BBB penetration ability by varying and controlling the size, surface composition and zeta potential of PEGylated MSNs. Those modifications, spatial arrangements, and charges make MSNs reveal characteristics including minimal non-specific binding, proper circulation period in physiological environment and transport thereof from blood to brain.

Inhibition of Cancer Metastasis

Cancer metastasis would result in high death rate of patients suffered from a cancer. Surprisingly, the inventors found that MSNs, which were usually used for delivering active ingredient only, may provide effects of inhibiting cancer metastasis, either in in vitro tests or in vivo tests with animal models. However, solid silica nanoparticles (SSNs), which are not mesoporous, cannot provide such effect. Without being bound to the theory, the porous structure of MSNs may contribute to the effect of inhibiting cancer metastasis, while the MSNs per se may not inhibit growth of tumors in situ.

Thus, a method of inhibiting cellular metastasis in a subject is provided herein, the method comprising administering a mesoporous silica nanoparticle (MSN) to the subject. In one embodiment, the MSNs have PEG surface modification to enhance the bioavailability. In one embodiment, the MSNs have both PEG and TA surface modification. In one embodiment, the MSNs have a particle size of 50 nm or less, preferably 30 nm or less. In one embodiment, the mesoporous silica nanoparticle has a BET surface area of 1000 $m^2/g$ or less, preferably 500 $m^2/g$ or less. In one embodiment, the cellular metastasis is carcinoma cell metastasis, e.g., lung carcinoma, breast cancer, colorectal cancer, melanoma, renal cancer, etc. In one embodiment, the route of administration is systemic or local administration. In one embodiment, the MSN is used with other chemodrugs or biological medicines respectively for combination therapy.

Pre-Coat of MSNs

Use of the protein corona contents for pre-coating the nanoparticles is an alternative way to direct their biodistribution or to avoid unwanted accumulation in non-targeting organs. The biological functions of all the common proteins related to the MSNs fate in vivo are be identified. One attempt is pre-coating MSNs with pre-treated plasma, the plasma being deprived of some specific proteins which are supposed to contribute to accelerated clearance of nanoparticles in blood. The other efforts is pre-coating MSNs with particular proteins found in the corona and having targeting ability, or that can facilitate the nanoparticles across the blood-brain barrier.

Examples of disease to be potentially treated based on the EPR effect and/or BBB penetration effect include, but are not limited to brain-associated cancer and Central Nervous System-associated cancer. Specific diseases include, but are not limited to acoustic neuroma, astrocytoma, chordoma, CNS lymphoma, craniopharyngioma, brain stem glioma, ependymoma, mixed Glioma, optic nerve glioma, subependymoma, medulloblastoma, meningioma, metastatic brain tumors, oligodendroglioma, pituitary tumors, primitive neuroectodermal (PNET), other brain-related conditions (cysts, neurofibromatosis, pseudotumorcerebri, tuberous sclerosis), schwannoma, juvenile pilocytic astrocytoma (JPA), pineal tumor, rhabdoid tumor.

Examples of the central nervous system-associated disease include, but are not limited to addiction, arachnoid cysts, attention deficit/hyperactivity disorder (ADHD), autism, bipolar disorder, catalepsy, depression, encephalitis, epilepsy/seizures, infection, locked-in syndrome, meningitis, migraine, multiple sclerosis, myelopathy, Alzheimer's disease, Huntington's disease, Parkinson's disease, Tourette's syndrome, Bell's palsy, cerebral palsy, epilepsy, motor neurone disease (MND), multiple sclerosis (MS), neurofibromatosis, sciatica, shingles, stroke.

An in vitro blood-brain barrier model is used for nanoparticle transport assays which is co-culture of brain capillary endothelial cells, brain pericytes and astrocytes to simulate in vivo BBB features. Furthermore, fluorescent-labelled MSNs are used to directly observe the particle accumulation in the brain vessel and brain tissue of mice by two photon fluorescence microscopy.

The following examples are provided to make the present invention more comprehensible to those of ordinary skill in the art to which the present invention pertains, but are not intended to limit the scope of the invention.

EXAMPLES

Materials, Methodologies and Test Models

Preparation of RITC-Conjugated APTMS

Conjugation of RITC to APTMS was achieved through the reaction between the isothiocyanate group in RITC) and the amino group in APTMS. RITC-conjugated APTMS used herein was prepared by adding 8 mg of RITC into 5 mL of ethanol, and then introducing 10 μL of APTMS into the ethanolic RITC solution; the mixture was stirred in the dark for at least 3 hours to give RITC-conjugated APTMS before they were utilized.

Transmission Electron Microscope (TEM)

Transmission electron microscopy (TEM) is used to directly examine and verify the appearance of the silica nanoparticles. The TEM images were taken on a Hitachi H-7100 transmission electron microscope operated at an accelerated voltage of 100 kV. Samples dispersed in ethanol were dropped on carbon-coated copper grids and dried in air for TEM observation.

Dynamic Light Scattering (DLS) and Zeta Potential

Size measurements of the silica nanoparticles in different solution environments were performed with Dynamic Light Scattering (DLS) on a Malvern Zetasizer Nano ZS (Malvern, UK). The (solvated) particle sizes formed in different solutions were analyzed: $H_2O$ and PBS buffer solution (pH 7.4) at room temperature. Surface charge (zeta potential) of the silica nanoparticles in aqueous solutions with different pH values were performed by a Malvern Zetasizer Nano ZS combined with MPT-2 titrator, and the sample solution was titrated from pH 6 to pH 8 and recorded the data at different pH points.

Elemental Analysis

The mass percentage of carbon, nitrogen, oxygen and hydrogen in silica nanoparticle were determined by elemental analyzer (elementar Vario EL cube type for NCSH, German).

In Vivo Imaging System (IVIS) for Detecting EPR Effect and Biodistribution of Nanoparticles In vivo biodistribution images of nanoparticles were obtained from IVIS imaging system (Lumina). The Balb/c mice (4-week old) were purchased from BioLASCO. The tumor-bearing mice were established by subcutaneous injection with 4T1 (ATCC®CRL-2539™) tumor cells for heterotopic implantation. After the 4T1 cells grew for 2-3 weeks, the sample in PBS was intravenously injected. After 24 hours from injection, the major organs (heart, lung, spleen, liver and kidney), tumor, urine and blood were carefully collected, and the fluorescence image and intensity of collected samples were acquired by the IVIS Imaging System.

The Blood-Brain Barrier (BBB) In Vitro Model

The in vitro BBB model is purchased from PharmaCo-Cell Company Ltd. (Nagasaki, Japan), which is established by triple cell co-culture, 12-well culture dishes containing transwell inserts with plated brain endothelial cells, pericytes and astrocytes. Prior to experiment, the BBB culture dish was incubated at 37° C. in 5% $CO_2$ condition for 4 days to make the tight-junctions between cells more compaction. Charge-modified MSN-PEG nanoparticles were suspended in 0.3 mL assay medium (0.33 mg/mL) and then added to the apical side of the BBB layers, culturing the model for 6 and 24 h. Furthermore, sodium fluorescein (Mw: 376; NaFluo) act as a non-specific transport marker. After culturing, the medium in the basolateral side was collected and Si concentration was detected by ICP-MS.

Two Photon Fluorescence Microscopy for Detecting Nanoparticles in Brain Vessel.

Healthy ICRmice (27-30 g) were intravenously injected with 200 mg/kg charge-modified MSN-PEG nanoparticles and dynamic imaging of the earlobe of mice was conducted by multi-photon microscopy (Olympus FVMPE-RS) with tunable excitation wavelengths (800-1000 nm). After nanoparticles were no longer circulated in the cerebral blood vessels, the mice were anaesthetized and skull-removed (craniotomy) procedure was then conducted. In this study, we use normal saline instead of placing cover glass on the surface of the brain for short-term observation. For imaging the blood vasculature, 0.6 mL of 2.5% (w/v) fluorescein isothiocyanate dextran (FITC-dextran, Mw: 70 kDa) dissolved in sterile saline I.V. injected into the mice. The depth profile imaging of charge-modified MSN-PEG nanoparticles in the mouse cerebrum were collected from 0 to 300 μm below the surface of the brain (axial spacing is 1 μm).

Pharmacokinetics and Quantification of Dox Accumulation

Healthy balb/c mice were single dose intravenously injected with Dox or Dox@NTT0_18 at 7.5 mg/kg. To determine the Dox concentration in plasma and brain, blood samples were taken at 15, 30, 60, 180, 360 and 1440 minutes after injection, and after the blood samples were taken, each animal was sacrificed and perfused with PBS to obtain the brain. Dox was extracted from the samples (plasma and brain respectively) for the determination of dox concentration with a spectrophotometer.

U87 Glioma Animal Model

U87-LUC glioma cells were cultured at 37° C. in a humidified 5% $CO_2$ atmosphere in minimum essential median (MEM) supplemented with 10% fetal bovine serum and 1% penicillin/streptomycin (Invitrogen). Cells were harvested by trypsinization, washed once with phosphate-buffered saline (PBS), and re-suspended ($1\times10^5$ cell/μL) in MEM for subsequent implantation into the striatum of mouse brains. Pathogen-free male NU/NU mice (5 to 7 weeks old) were purchased from BioLASCO (Taiwan). Mice were housed and maintained in a controlled environment and all procedures were performed in accordance with the experimental animal care guidelines of the Animal Committee of Chang Gung University. To implant U87-LUC tumor cells, animals were anesthetized with 2% isoflurane gas and immobilized on a stereotactic frame. A sagittal incision was made through the skin overlying the calvarium, and a 23 G needle was used to create a hole in the exposed cranium 1.5 mm anterior and 2 mm lateral to the bregma. Five microliters of U87-LUC glioma cell suspension were injected at a depth of 2 mm from the brain surface. The injection was performed over a 3-minute period, and the needle was withdrawn over another 2 minutes. The growth of the brain tumor was monitored by IVIS and MRI.

Example 1

Preparation of Mesoporous Silica Nanoparticles with Various Ratios of PEG to Functional Groups Modification on Nanoparticle Surface Mesoporous silica nanoparticles (MSNs) possess a well-defined structure and high density of surface silanol groups which can be modified with a wide range of organic functional groups. The MSNs of different size were prepared using an ammonia base-catalyzed method under highly dilute and low surfactant conditions. The particle size was controlled by adjusting ammonia concentration, TEOS amount added, and reaction temperature. TA-silane (N-[3-(trimethoxysilyl)propyl]-N,N,N-trimethylammonium chloride) was used as the exemplified charge modulating agent for providing positively charged groups on the surface of the MSNs. Typically, 0.29 g of CTAB was dissolved in 150 mL of ammonium hydroxide solution (0.1-0.2M) at the desired temperature (50-60° C.) in a sealed beaker. After 15-minutes of stirring, the sealed membrane was removed, and then 2.5 mL of ethanolic RITC-conjugated APTMS and 2-2.5 mL of ethanolic TEOS (0.8-0.9M) were added to the solution under vigorous stirring (600 rpm). After 1 hour of stirring, the 550 μL of PEG-silane (2-[methoxy(polyethyleneoxy)propyl]-trimethoxysilane) with different molar ratio of PEG-silane to TA-silane (the ratio of PEG-silane/TA-silane=15:1, 10:1, 7:1, 3:1, 2:1, 1:2; the amount of TA-silane is 0.04-1.2 mL) in 2 mL of ethanol was introduced into the reaction. After the mixture was stirred for 30 minutes, the mixture was aged at desired temperature (50-60° C.) without stirring for at least 12 hours. And then the solution was sealed and placed in an oven at 70° C. for 24 hours of hydrothermal treatment. The as-synthesized sample was washed and collected by centrifugation or cross-flow system. For removing the surfactant in the pores of the MSNs, the as-synthesized sample was incubated in 40 mL of acidic ethanol containing 678 μL (first time) and 40 μL (second time) of hydrochloric acid (37%) for 1 hour of extraction respectively at 60° C. The products were washed and harvested by centrifugation or cross-flow system and finally stored in 90% ethanol. For a different functional group modified MSN-PEG synthesis, the TA-silane was replaced with PEI-silane, EDPTMSN-silane or other functional-silanes.

Example 2

TEM and DLS Measurements

Figure 1B:
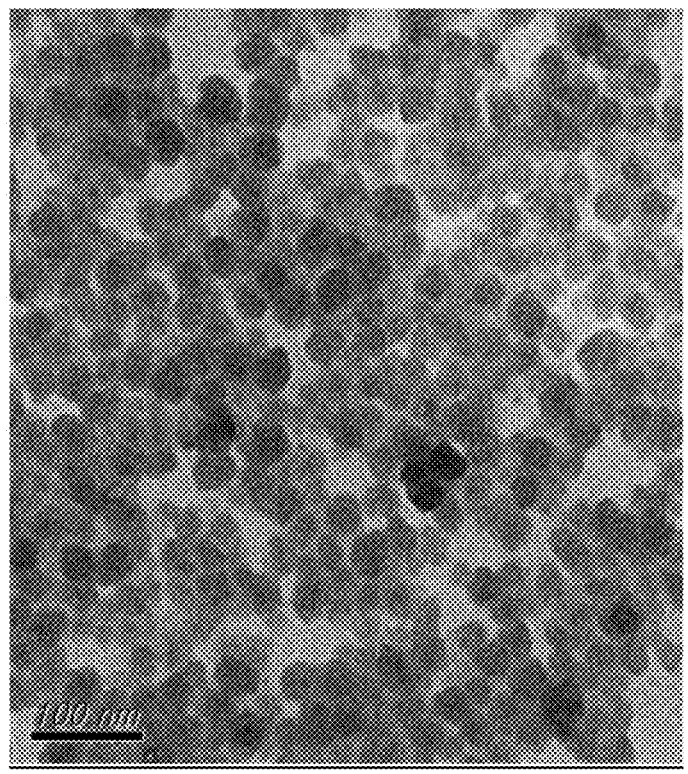

The MSNs as synthesized in Example 1 were subject to TEM measurements, and the results are shown in FIG. 1. The particle sizes and standard deviations thereof are shown in Table 1. TEM results suggest that 30 nm MSNs with various modifications have an average particle size of around 25 to 35 nm, and 50 nm MSNs with various modifications have an average particle size of around 40 to 60 nm, both with small standard deviations of particle size, which reflect the uniformity of the particles.

TABLE 1

| 30 nm R-MSNs | TEM Size ± SD(nm) | 50 nm R-MSNs | TEM Size ± SD(nm) |
|---|---|---|---|
| PEG only | 30.2 ± 3.6 | PEG only | 44.2 ± 4.9 |
| PEG/TA 15:1 | 25.9 ± 3.8 | PEG/TA 7:1 | 39.4 ± 3.6 |
| PEG/TA 10:1 | 29.7 ± 3.8 | PEG/TA 3:1 | 36.0 ± 3.4 |
| PEG/TA 7:1 | 30.8 ± 3.3 | PEG/TA 2:1 | 42.5 ± 5.5 |
| PEG/TA 3:1 | 30.2 ± 2.6 | PEG/TA 1:2 | 41.5 ± 4.7 |
| PEG/TA 2:1 | 29.4 ± 3.2 | TA only | 37.3 ± 3.8 |
| PEG/TA 1:2 | 29.1 ± 3.2 | PEG/EDPTMS | 50.5 ± 4.7 |
| TA only | 29.0 ± 4.4 | PEG/PEI | 53.5 ± 5.0 |
| PEG/THPMP | 21.0 ± 3.3 | | |
| PEG/PEI | 30.7 ± 3.5 | | |

The particle size of the MSNs with various modifications measured via Dynamic Light Scattering (DLS) in different solution environments is shown in Table 2. DLS results show that all MSNs dispersed well within the range from about 35 nm to 45 nm or 50 nm to 70 nm in buffer.

TABLE 2

| 30 nm R-MSNs | DLS Size (nm) in H$_2$O/PBS | 50 nm R-MSNs | DLS Size (nm) in H$_2$O/PBS |
|---|---|---|---|
| PEG only | 38.3/38.8 | PEG only | 66.4/62.4 |
| PEG/TA 15:1 | 38.5/45.8 | PEG/TA 7:1 | 55.2/58.4 |
| PEG/TA 10:1 | 37.4/44.2 | PEG/TA 3:1 | 59.7/62.5 |
| PEG/TA 7:1 | 37.8/38.9 | PEG/TA 2:1 | 56.0/58.3 |
| PEG/TA 3:1 | 36.8/38.2 | PEG/TA 1:2 | 54.7/68.8 |
| PEG/TA 2:1 | 36.2/37.5 | TA only | 53.9/55.9 |
| PEG/TA 1:2 | 35.7/37.2 | PEG/EDPTMS | 51.2/65.7 |
| TA only | 36.5/46.5 | EPG/PEI | 56.2/66.7 |
| PEG/THPMP | 31.9/30.8 | | |
| PEG/PEI | 37.6/40.4 | | |

Elemental Analysis

In the MSN-PEG+TA synthesis process, PEG silane and TA silane at different molar ratios were used for the reaction for modulating the PEG/TA ratio on MSN. For quantifying the functional group on MSN-PEG+TA nanoparticles, the elemental composition of MSN-PEG+TA particles was measured by elemental analyzer. The mole ratio of PEG group to TA group (PEG/TA) on MSN-PEG+TA is derived from the mass percent of nitrogen and carbon of MSN-PEG+TA particles. The PEG/TA ratio of MSN-PEG+TA (1:2), (2:1) and (10:1) derived from elemental analysis is about 0.64, 2.67, and 6.13.

Example 3

Figure 2:
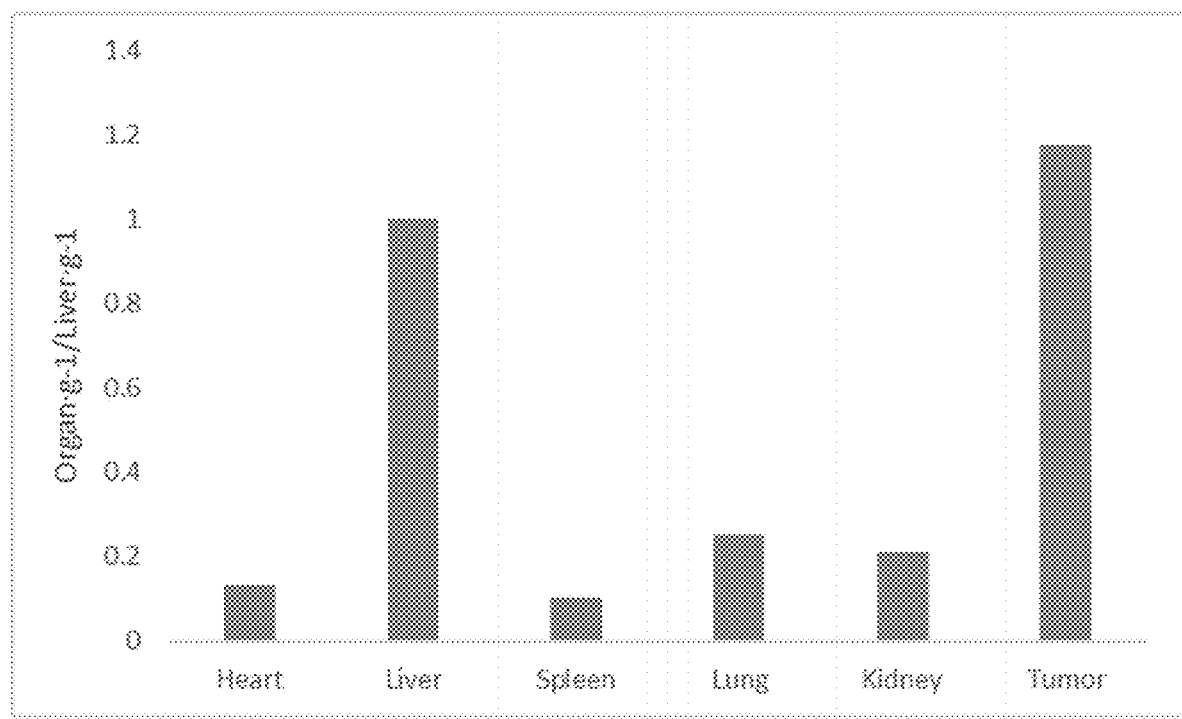

Effect of Surface Charge and Spatial Arrangement of Functional Groups on Biodistribution and Tumor Targeting Ability It is demonstrated that an MSN shows excellent tumor targeting ability based on EPR effect and there are several key determinants should be considered: (1) The particle size is smaller than 100 nm, preferably ranging from about 20 nm to 50 nm, e.g., about 30 nm; (2) the exterior surface should be covered by PEG and any modifications should be hidden within the PEG layer; (3) the surface charge and PEG/charge modulating moiety ratio should be confined in a specific range. To evaluate the effect of spatial arrangement of functional group on EPR effect, we synthesized MSNs with similar size and zeta potential but different length or molecular weight of positively charged molecule. The PEG for MSN PEGylation is MW 459-591 and positively charged group for surface modification is trimethoxysilylpropy 1-modified polyethyleneimine (PEI-silane, MW=1500-1800), N-trimethoxysilylpropyl-N,N,N-trimethyl ammonium chloride (TA-silane, MW=258), or N-[3-(Trimethoxysilyl)propyl]ethylenediamine (EDPTMS, MW=222). The higher molecular weight PEI-silane is expected to be exposed on the exterior surface beyond the PEG layer, but TA- and EDP-silane have smaller molecule weight compared to PEG-silane, thereby shorter chain length, so the quaternary amine of TA and primary and secondary amine of EDP are expected to be hidden within the PEG layer. The synthetic diameter (TEM), hydrodynamic diameter in water and buffer (DLS) and zeta potential of MSN-PEG+PEI, MSN-PEG+TA and MSN-PEG+EDP are nearly identical (Table 3). The EPR effect of these particles was examined by injecting the particles through the tail vein into a tumor-bearing mouse. One day after injection, the particle accumulation in tumor and organs were determined by IVIS. MSN-PEG+TA and MSN-PEG+EDP revealed strong fluorescence signal in tumor and the ratio of signal of tumor to the signal of liver is higher than 3. This demonstrates that the particles accumulate in tumor and have excellent EPR effect. However, even though the MSN-PEG+PEI has similar size and zeta potential with MSN-PEG+TA, but MSN-PEG-PEI do not accumulate in tumor. (Table 3). Besides hiding the functional groups within PEG layer, the surface charge of MSN is also important for modulating the EPR effect. Although it is well known that PEGylation can improve the blood circulation and accumulation within tumors, the improvement is insufficient. The ratio of particle accumulation in tumor to liver (tumor/liver) is about 1.2 for 30 nm MSN-PEG and 0.35 for 50 nm MSN-PEG (FIG. 2).

Figure 3:
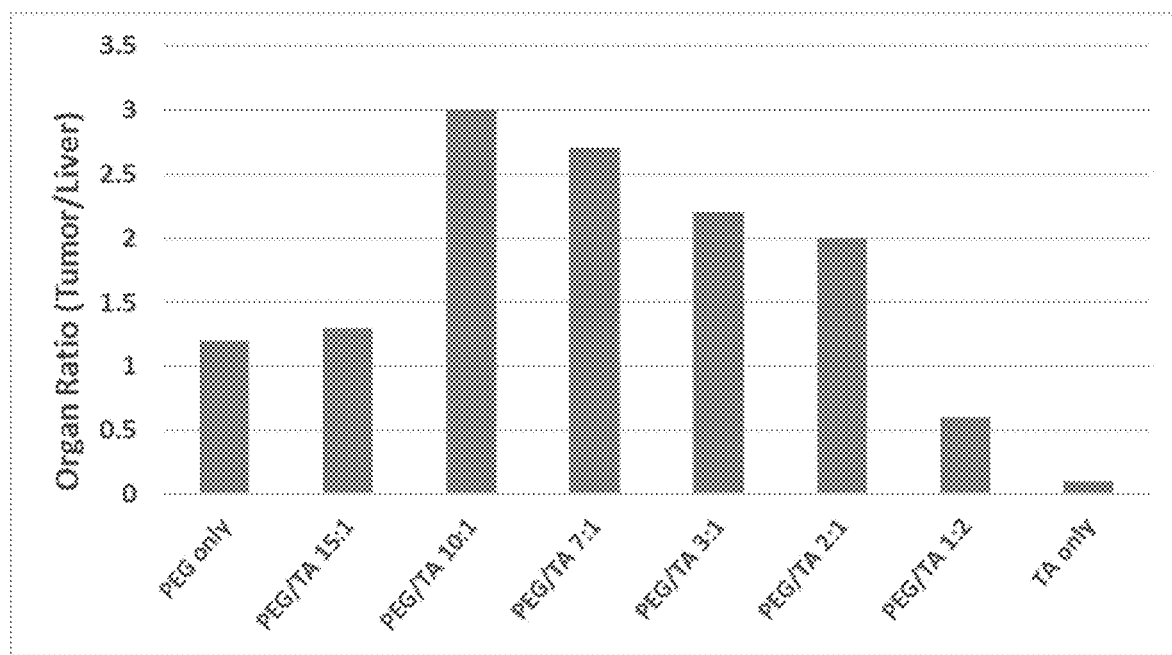

Introducing a different molar ratio of PEG to TA (PEG/TA) in a synthesis process for modulating the composition of functional groups on the surface and zeta potential can also significantly enhance the EPR effect. The particle accumulation ratio value (tumor/liver) rises to 2-3, representing a 2 to 8.6 fold improvement. The 30 nm MSN-PEG+TA nanoparticles modified with the PEG/TA in the ratio from 15:1 to 2:1 (PEG-silane/TA-silane in synthesis process) having zeta potential (in pH 7.4 condition) increasing from −15 to +7 mV reveal a higher particle accumulation ratio value (tumor/liver) than MSN-PEG, MSN-TA (zeta potential: +31), and PEG/TA (1:2) modified nanoparticles (zeta potential: +21) (FIG. 3). A similar result was obtained when the MSN-PEG+TA particle size is 50 nm and has a PEG/TA ratio from 7:1 to 2:1 and zeta potential (in pH 7.4 condition) increasing from +12 to +18 mV; the particles showed better tumor targeting ability than 50 nm MSN-PEG. The results reveal that the surface charge and PEG/TA ratio of MSN-PEG+TA in a specific range can enhance the tumor targeting ability of nanoparticle.

TABLE 3

| 50 nm MSNs modification with | DLS (d, nm) $H_2O$ | DLS (d, nm) PBS | Zeta Potential (mV) at pH 7.4 | EPR (Tumor/Liver Ratio) |
|---|---|---|---|---|
| PEG only | 65.6 | 62.4 | −21.0 | 0.35 |
| PEG + TA-silane | 55.2 | 58.3 | +18.0 | 3.09 |
| PEG + EDPTMS | 52.6 | 59.5 | +19.5 | 3.50 |
| PEG + PEI-silane | 58.2 | 66.7 | +21.0 | 0.04 |

Example 4

Effect of Surface Charge on Blood-Brain Barrier Penetration Capability

Figure 4A:
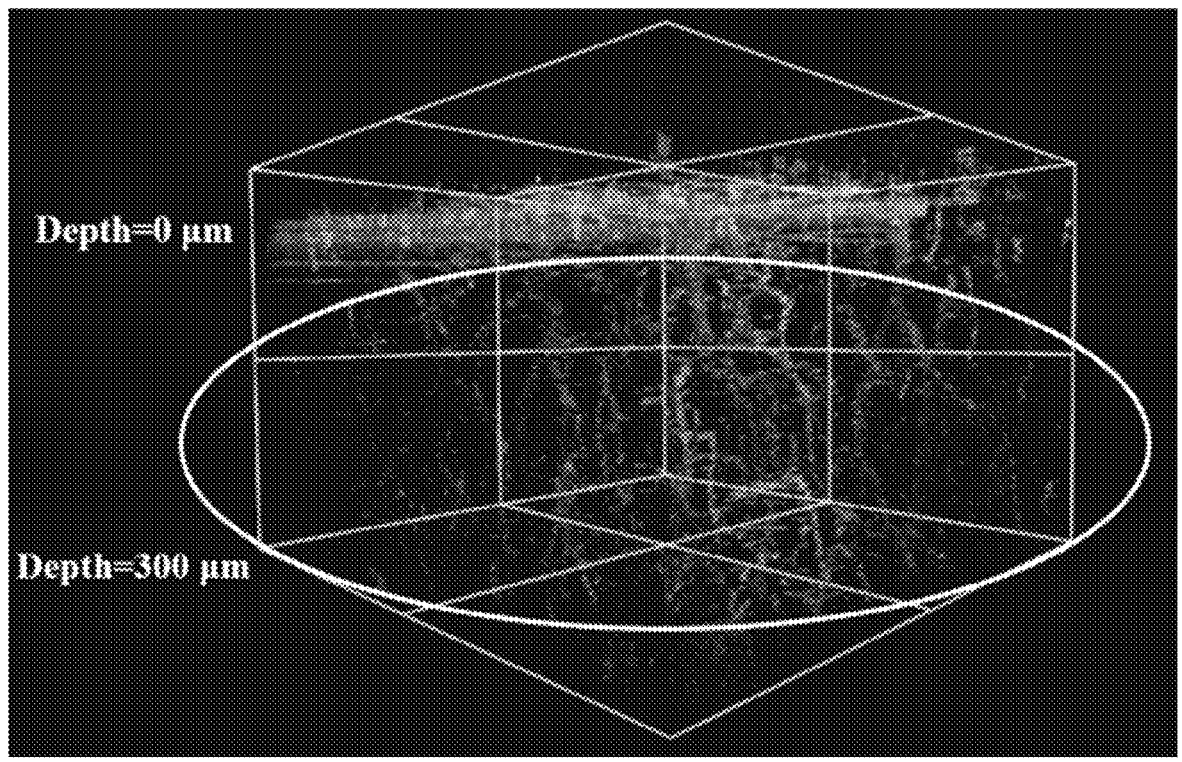

Delivery of therapeutic drug into the brain is still a major challenge because of the BBB nanoparticles smaller than 100 nm provide advantages in improving drug transport across the BBB. In this invention, we demonstrated the effect of size, composition and zeta potential of PEGylated MSN on BBB penetration in vitro and in vivo. We synthesized three different sizes (10, 30, 50 nm) of MSN with different surface modifications to quickly screen the particles with BBB penetration ability with a BBB kit, which is an in vitro BBB model made of primary cultures of rat (Wistar rat) brain capillary endothelial cells, brain pericytes and astrocytes. The 30 nm PEGylated MSN modified with positively charged TA molecule on the surface revealed relatively effective crossing through the cell layers of BBB in vitro assay. To understand BBB penetration capability of the nanoparticles in vivo, we used two-photon fluorescence spectroscopy to monitor the distribution of nanoparticles in vessels of the brain in mouse. The fluorescent-labelled nanoparticles were administrated through tail vein. Two days after injection, we detected brain vessels located within a depth of 0-300 μm from the surface. Meanwhile, FITC-dextran was injected through i.v. for mapping the angio-architecture and revealing the boundary of blood vessel walls. If the fluorescence signal from nanoparticles overlaps with the FITC-dextran's signal (green signal), it will appear yellow signal otherwise it will be red, meaning that the nanoparticle is not in the blood vessel, and may have crossed the BBB into the brain tissue. The 3D images of brain vessel showed numerous red signals from MSN-PEG+TA nanoparticles distributed in the blood vessel wall and brain tissue area (FIG. 4A). The distribution of MSN-PEG+TA in brain was further determined by observing the dispersion pattern of nanoparticles in brain tissue sections. Nanoparticles were detected at different locations in the brain tissue.

Figure 4B:
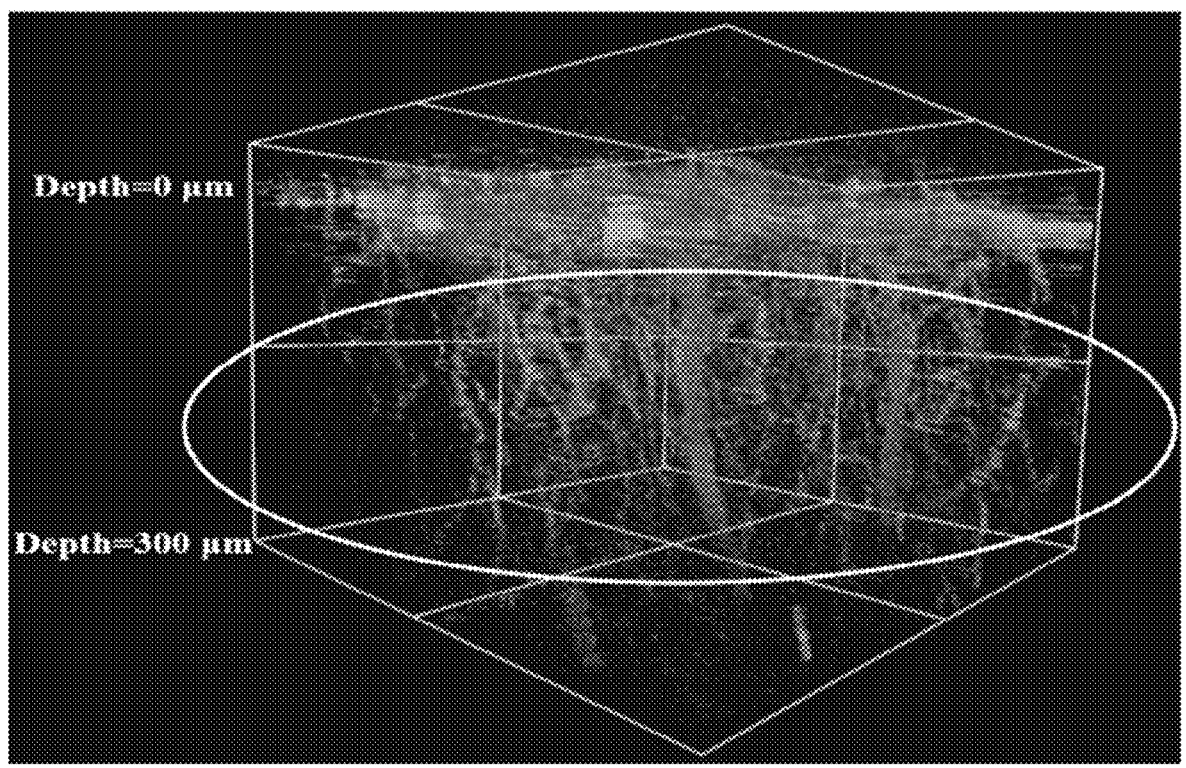

The results indicate that 30 nm MSN-PEG+TA with a specific range of PEG/TA ratio (10:1 to 2:1) modifications exhibited potential to cross the BBB into the brain tissue. However, negatively charged THPMP molecule modified nanoparticles (MSN-PEG+THPMP) did not reveal BBB penetration capability (FIG. 4B). To exhibit BBB penetration in vivo a nanoparticle must possess minimal non-specific binding and proper circulation time under physiological environment. Furthermore, the physicochemical properties of nanoparticles determinative of the passage mechanism across the BBB. Although mechanisms of nanoparticles crossing the BBB have been described, including receptor or absorptive mediated transcytosis by endothelial cells and opening of the tight junctions between endothelial cells, it is still hard to develop a nanoparticle with BBB penetration capability for bioapplications. In this invention, we demonstrated that hiding the functional groups (TA molecule) within the PEG layer and modulating the PEG/TA ratio (10:1 to 1:2, preferably ranging from about 10:1 to 2:1) on the surface to vary the zeta potential (in pH 7.4 condition) between −13 to +21 mV (preferably ranging from about −13 to +7 mV) can confer the nanoparticle the ability to penetrate the BBB for delivering drug into brain for CNS disease and brain tumors.

Example 5

Pharmacokinetics of Dox and Dox@MSN-PEG+TA in Plasma and Brain

For preliminary quantification of MSN-PEG+TA blood circulation time prolongation and BBB penetration enhancement, we analyzed the pharmacokinetics of a chemodrug, doxorubicin (Dox) with or without MSN-PEG+TA encapsulated. Mice received a single dose of Dox or Dox@NTT0_18 (MSN-PEG+TA-loaded Dox) through intravenous injection (all at Dox dose 7.5 mg/kg). To determine the Dox concentration in plasma and brain, blood samples were taken at 15, 30, 60, 180, 360 and 1440 minutes after injection and animals were sacrificed and perfused with PBS at each time point. Dox was extracted from plasma and brain and the Dox concentration was measured using a spectrophotometer. The concentration versus time curves of Dox in plasma with and without MSN-PEG+TA encapsulated was also established. After injection of Dox solution, Dox concentration was hardly detectable in plasma after 15 minutes (lower than 0.2 μg/mL); however, Dox was still present after 6 hours in the mouse injected with Dox@NTT0_18. Brain analysis in these perfused mice showed that administration of Dox@NTT0_18 has 2-6.6 fold higher Dox accumulation in the brain compared to administration of Dox solution. These results demonstrated that the Dox encapsulated in MSN-PEG+TA nanoparticle can prolong blood circulation time and enhance permeability of BBB.

Example 6

Dox@MSN-PEG+TA for Brain Tumor Therapy

The 30 nm MSN-PEG+TA particle possesses tumor targeting (EPR effect) and BBB penetration properties which provide advantages for MSN-PEG+TA nanoparticle as a drug delivery nanocarrier for brain tumor therapy. Dox is a well-known anti-cancer drug approved for treatment of multiple cancers. Dox shows activity against glioma cells in vitro but has been unable to cross the BBB into the brain. Moreover, Dox is not approved for brain cancer therapy. Our MSN-PEG+TA nanoparticle provides the opportunity to deliver Dox into brain for brain cancer therapy. The Dox@MSN-PEG+TA was synthesized by incubating Dox with MSN-PEG+TA solution for 1 hour, it was washed twice with water to remove the unencapsulated Dox and collected by centrifugation. To evaluate the efficacy of Dox@MSN-PEG+TA anti-brain tumor in vivo, the U87-LUC brain cells were implanted orthotopically into nude mice to serve as the U87-LUC xenograft mouse model; U87-LUC cells can express luciferase for quantification of tumor cells in vivo. Four days after tumor implantation, the same Dox dosage (10 mg/kg) of free Dox and Dox@MSN-PEG+TA and about 250 mg/kg MSN-PEG+TA were administrated respectively through tail vein into U87-LUC xenograft mouse model every 4 days for 3 times, and body weight and tumor size were examined during the study period. Although the tumor size of Dox and Dox@MSN-PEG+TA shrunk during the treatment period, the high toxicity of Dox weakens the mice weak and causes death of the host. In contrast, the mice treated with Dox@MSN-PEG+TA showed body weight reduction during the therapeutic period but recovered after dosing was stopped. The MM images of mouse brain of the Dox@MSN-PEG+TA treatment group exhibit significant tumor shrinkage on day 13, and the tumor was nearly undetectable on day 34, with an empty space revealed in its place (figure not shown). The survival time of the mice treated with Dox@MSN-PEG+TA was significantly prolonged because of the tumor disappearance. For evaluating the EPR and BBB penetration capability of MSN-PEG+TA and Dox@MSN-PEG+TA, the mice were sacrificed at 24 h after last injection and then the brain was collected and fixed for preparing frozen sections. The distribution of MSN-PEG+TA and Dox@MSN-PEG+TA in brain tissue and tumor were assessed from the tumor sections from nanoparticle treated mice. The DAPI was used to stain the nuclei of cells and the tumor tissue was identified by area of hypercellularity from DAPI stained cell. Mice treated with MSN-PEG+TA showed a lot of nanoparticle accumulation in the center and periphery of the tumor. This phenomenon may due to the combination of both EPR effect and BBB penetration properties of MSN-PEG+TA (figure not shown). The brain section of mice treated with Dox@MSN-PEG+TA showed that the tumor area is much smaller than the PBS group because of the anti-brain tumor efficacy of Dox@MSN-PEG+TA. There is an obvious difference between MSN-PEG+TA and Dox@MSN-PEG+TA. The Dox@MSN-PEG+TA not only accumulated in tumor area but also appeared in non-tumor areas; the signal of Dox@MSN-PEG+TA can be detected in various areas of the whole brain (figure not shown). These results demonstrate that when the leaky vasculature formed during tumor growth, the EPR effect of Dox@MSN-PEG+TA will dominate biodistribution and deliver Dox to the tumor area to kill the tumor cells and shrink the tumor. Once the tumor shrinks and the EPR effect is weakened, the phenomenon of Dox@MSN-PEG+TA nanoparticles crossing BBB is easier to observe. In clinical cases, cancer cells at the periphery of the tumor may infiltrate into normal brain tissue that will make therapeutic drug delivery difficult because the BBB and blood vessels in the area are intact to block drugs from the area. The BBB penetration property of Dox@MSN-PEG+TA has the capability to deliver Dox into the BBB intact area to kill the infiltrating cancer cells or kill the remaining cancer cells after tumor removal surgery. Therefore, MSN-PEG+TA containing both EPR and BBB penetration capability as a drug delivery system shows advantages in treatment of cancers, especially brain associated cancers and CNS diseases.

The ingredients, reaction conditions and parameters illustrated in the examples are merely for illustrative purposes and not intended to limit the material or the preparation method.

Examples of the brain-associated cancer and Central Nervous System-associated cancer include but are not limited to acoustic neuroma, astrocytoma, chordoma, CNS lymphoma, craniopharyngioma, brain stem glioma, ependymoma, mixed Glioma, optic nerve glioma, subependymoma, medulloblastoma, meningioma, metastatic brain tumors, oligodendroglioma, pituitary tumors, primitive neuroectodermal (PNET), other brain-related conditions (cysts, neurofibromatosis, pseudotumor cerebri, tuberous sclerosis), schwannoma, juvenile pilocytic astrocytoma (JPA), pineal tumor, rhabdoid tumor.

Examples of the central nervous system-associated disease include but are not limited to addiction, arachnoid cysts, attention deficit/hyperactivity disorder (ADHD), autism, bipolar disorder, catalepsy, depression, encephalitis, epilepsy/seizures, infection, locked-in syndrome, meningitis, migraine, multiple sclerosis, myelopathy, Alzheimer's disease, Huntington's disease, Parkinson's disease, Tourette's syndrome, Bell's palsy, cerebral palsy, epilepsy, motor neurone disease (MND), multiple sclerosis (MS), neurofibromatosis, sciatica, shingles, and stroke.

Example 7

In Vitro Tests of Inhibiting Cancer Cell Metastasis

Wound healing assay is adopted for evaluating the potential of inhibiting cancer metastasis with treatment of MSNs. The MSNs particles with various surface modifications or particle sizes are used for the assay; solid silicate nanoparticles (SSNs), i.e., nanoparticles substantially having no pores thereon, are also used for the assay as comparative examples. The wound healing assay is operated as following process: the ibidi Culture-Inserts 2 Well were transferred to 24-well plates and the 4T1 cells ($2\times10^4$ cells/well) were seeded into the two compartments of Culture-Inserts for 24 hours. After incubation, the insert was removed and a uniform wound was made. The wells were washed twice with PBS to remove the detached cell, and cells were cultured in RPMI medium with 1% FBS and 200 µg/mL MSNs or SSNs. Images were acquired at 0, 16, 24 hours by microscope and the wound area healing ratio was counted by ImageJ. Details of the parameters are shown in Table 4 below:

TABLE 4

| Particle Size | Particle Type |
|---|---|
| 25 nm | MSN-PEG |
| 25 nm | MSN-PEG + TA |
| 50 nm | MSN-PEG |
| 50 nm | MSN-PEG + TA |
| 50 nm | MSN-PEG + PEI |
| 50 nm | SSN-PEG |

Figure 5A:
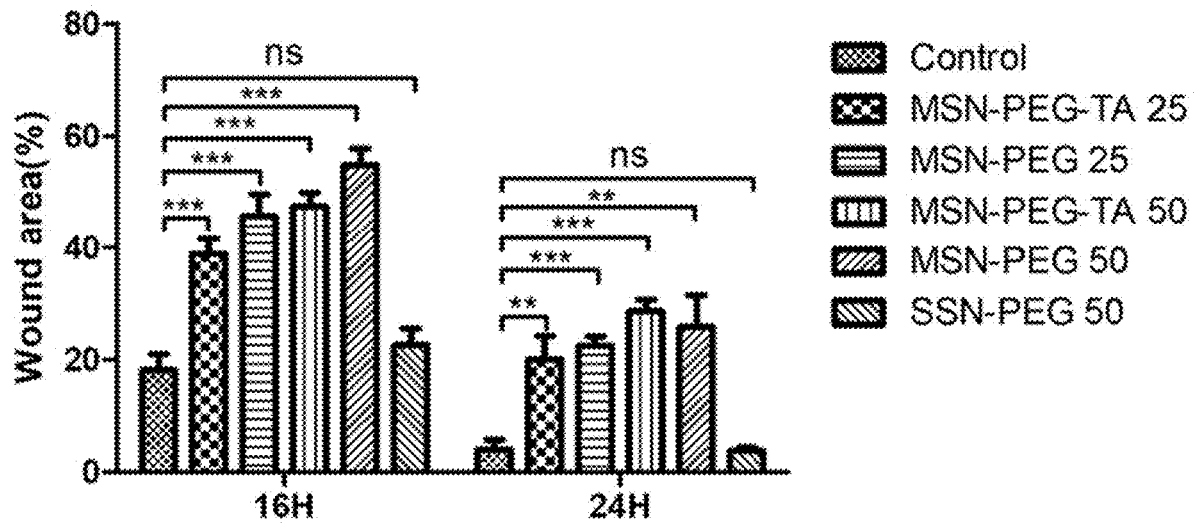
FIG. 5A and FIG. 5B show the results of in vitro tests for evaluating the effect of inhibiting cellular migration.

FIG. 5A shows the comparison of wound area percentage for each sample after 16 hours and 24 hours; results revealed that MSNs (having mesopores) with various surface modification and sizes can exhibit effects of inhibiting cellular migration, while SSNs cannot provide such effect.

Figure 5B:
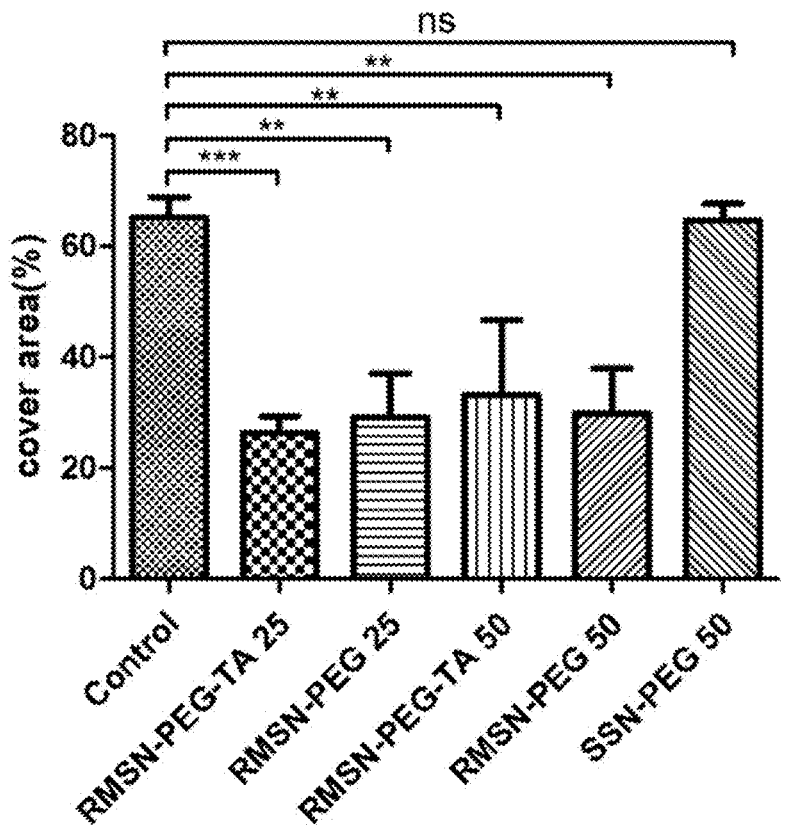

Boyden Chamber Assay is also adopted for evaluating the potential of inhibiting cancer metastasis with treatment of MSNs. For evaluating the MSNs inhibit cellular migration capability, $2 \times 10^5$ 4 T1 cells/well were seeded in 6-well plate for 24 hours, after that cells were treated with 200 µg/mL MSNs or SSNs for 24 hours. Then the cells were harvested and transferred into the upper side of boyden chamber ($7 \times 10^4$ cells/well), the boyden chamber assay uses a hollow plastic chamber, sealed at one end with a porous membrane and chamber is suspended over a well and contain RPMI medium. Cells were placed into the upper side of chamber and allowed to migrate through the pores, to the other side of the membrane. After 24 hours, the cells were fixed by 4% formaldehyde solution and stain with 0.5% crystal violet. The nonmigrated cells on the upper side of the chamber were removed with cotton swab and the images of migrated cells were taken by microscope. FIG. 5B shows the comparison of cell cover area percentage at the lower layer (Migratory cells) for each sample; results revealed that MSNs (having mesopores) with various surface modification, including PEG modification and PEG in combination with TA modification as noted above, and sizes may exhibit effects of inhibiting cellular migration, while SSNs cannot provide such effect. Such results may serve as evidence that the mesoporous of the silica nanoparticles can provide contribution to the effect of inhibiting cellular metastasis.

Example 8

In Vivo Tests on Mice

In vivo tests on mice were conducted for evaluating the therapeutic effect of MSNs. BALB/c mice implanted with $1.5 \times 10^6$ luciferase-4T1 cancer cells (luciferase labelled breast cancer cells) on their back are used as the in vivo test model. In this spontaneous cancer metastasis model, the cancer cells spread from transplanted site to secondary site (site of metastasis: lung, lymph node, etc.) upon the implanted tumor growth. Mice were intravenously administered (I.V.; 200 mg/kg) or intratumoral administered (I.T.; 20 mg/kg) with 25 nm MSN-PEG-TA on day 12, 15, and 18. For tracking the cancer metastasis, luminescence diagrams were taken by IVIS system on days 21, 28, 32, 35. On day 35, the lung of mice was enucleated and then dyed with India ink. The tumor tissue emerged as white nodules on the black lungs after a few minutes. The tumors were counted to determine the level of metastasis. Body weights of mice and tumor volume were measured twice a week.

Figure 6A:
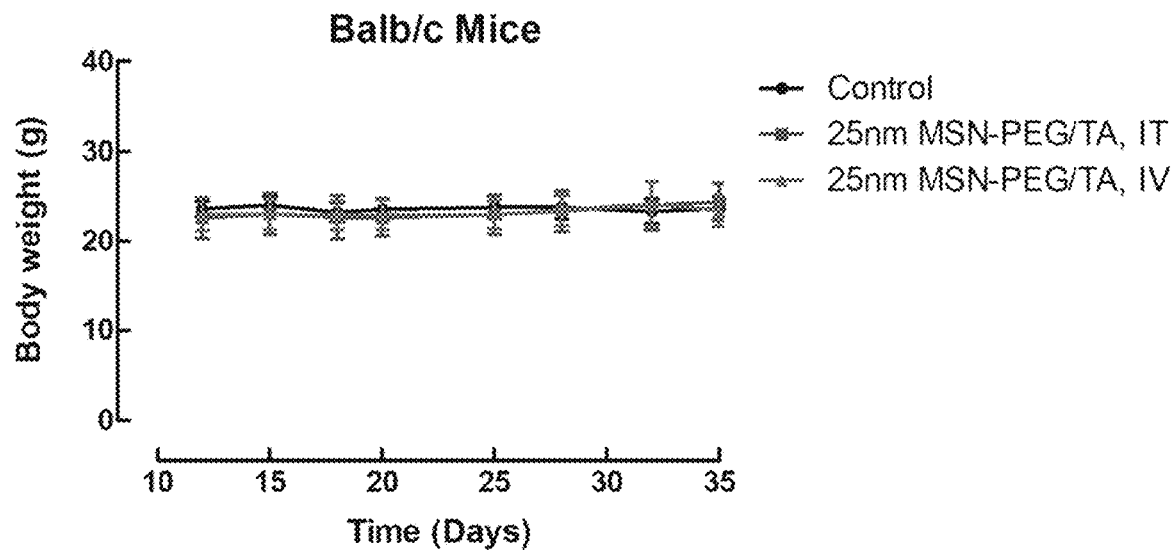
FIG. 6A and FIG. 6B show the results of in vivo tests for evaluating the toxicity of MSNs to mice.
Figure 6B:
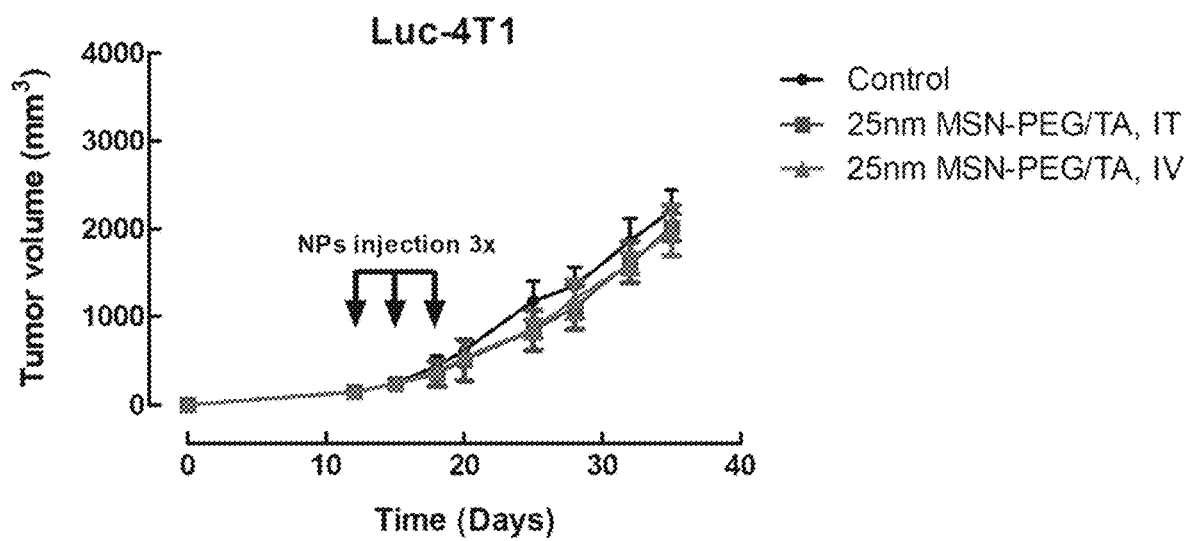

FIG. 6 shows that the body weight of mice measured in each group maintains nearly constant, which means that MSN-PEG-TA may not be toxic to mice. On the other hand, the tumor volume measured on different days revealed that MSN-PEG-TA may not inhibit growth of tumor in situ.

Figure 7:
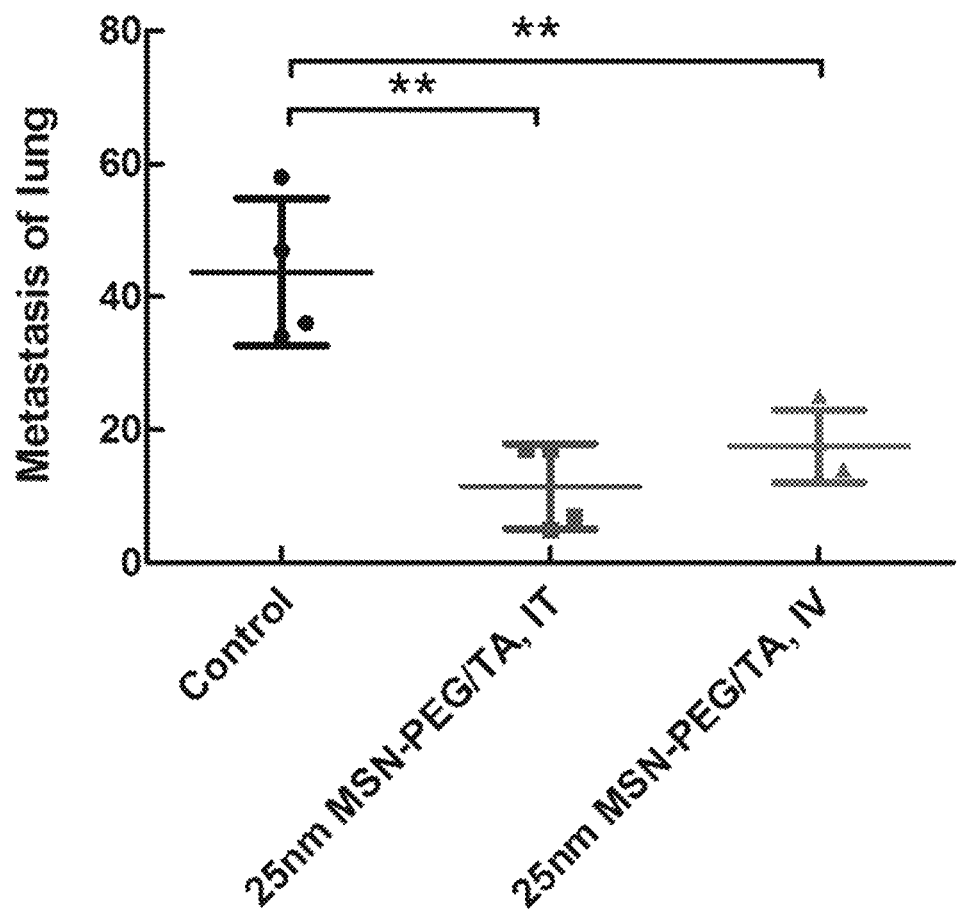
FIG. 7 shows the results of in vivo tests for evaluating the effect of inhibiting breast cancer metastasis to lung.

FIG. 7 shows the result of level of cancer metastasis to lung, which revealed that both I.V. and I.T. administrations of MSN-PEG-TA can inhibit the metastasis.

Figure 8:
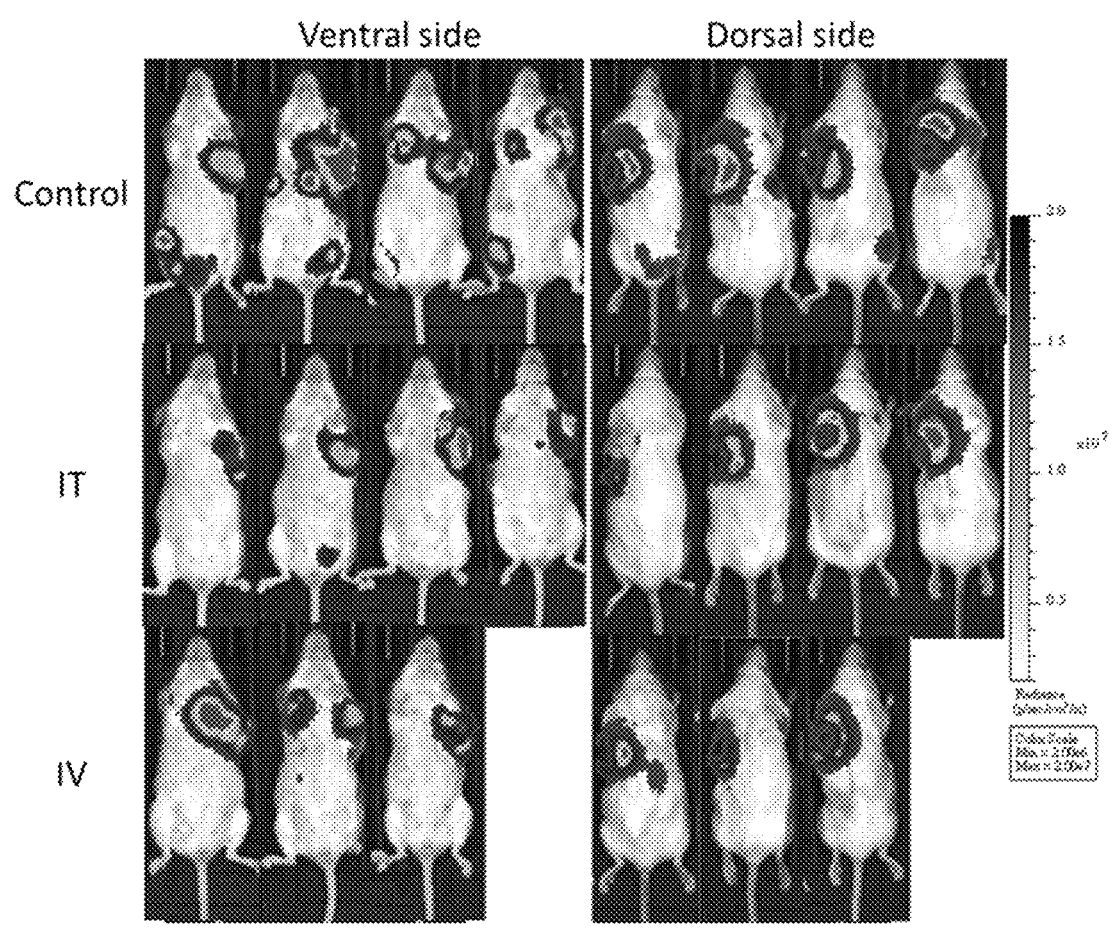
FIG. 8 shows the result of luminescence diagrams for evaluating the effect of inhibiting cancer metastasis

FIG. 8 shows the result of luminescence diagrams reveal that mice with I.V. or I.T. administration of 25 nm MSN-PEG-TA have a lower level of metastasis from back to other parts of the body (such as lung and lymph node) than the mice in the control group.

A person of ordinary skill in the art of the subject invention should understand that variations and modification may be made to the teaching and the disclosure of the subject invention without departing from the spirit and scope of the subject application. Based on the contents above, the subject application intends to cover any variations and modification thereof with the proviso that the variations or modifications fall within the scope as defined in the appended claims or their equivalents.

We claim:

1. A mesoporous silica nanoparticle, comprising an organic modification on a surface thereof, having a zeta potential within the range from about −22 mV to about +25 mV at pH 7.4 and a particle size of about 50 nm or less, wherein the organic modification comprises a poly(ethylene glycol) (PEG) moiety and at least one of positively charged group containing molecule/oligomer/polymer, wherein the positively charged group containing molecule/oligomer/polymer is hidden within the PEG moiety, wherein the molar ratio of the poly(ethylene glycol) moiety to the positively charged group containing molecule/oligomer/polymer lies within the range from 15:1 to 1:2.

2. The mesoporous silica nanoparticle according to claim 1, wherein the particle size is about 30 nm or less.

3. The mesoporous silica nanoparticle according to claim 1, wherein the zeta potential is within the range from about −15 mV to about +7 mV at pH 7.4.

4. The mesoporous silica nanoparticle according to claim 1, wherein the organic modification is derived by substances selected from poly(ethylene glycol) (PEG), poly(propylene glycol) (PPG) and PEG-PPG copolymers.

5. The mesoporous silica nanoparticle according to claim 1, wherein the surface of the nanoparticle comprises further modification derived from at least one surface modifying agent selected from polyethylenimine (PEI); alkoxylsilane-terminated (poly)alkylene(poly)amine; organo-alkoxysilane; or zwitterionicsilane.

6. The mesoporous silica nanoparticle according to claim 1, wherein the molar ratio of the poly(ethylene glycol) moiety to the positively charged group containing molecule/oligomer/polymer lies within the range from about 15:1 to about 2:1 or about 10:1 to about 2:1 or about 6.5:1 to about 2:1.

7. The mesoporous silica nanoparticle according to claim 1, wherein the nanoparticle further comprises a bioactive ingredient loaded onto and/or into it.

8. The mesoporous silica nanoparticle according to claim 7, wherein the bioactive ingredient is selected from a small molecule drug, a protein, an antibody, a vaccine, an antibiotic or a nucleotide drug.

9. A method for preparing a mesoporous silica nanoparticle (MSN) with surface modification, comprising the steps of:
   (a) providing an alkaline solution containing a surfactant at a concentration sufficient for forming micelles;
   (b) introducing silane source(s) into the solution;
   (c) introducing surface modifying agents comprising at least one PEG-modified silane and at least one positively charged group containing silane into the solution;

the mole ratio of PEG-modified silane to positively charged group containing silane lies within a range from 15:1 to 1:2

(d) conducting hydrothermal treatment to the solution;
(e) collecting the products;
(f) removing the residual surfactant(s) from the products; and optionally
(g) purifying or cleaning the products.

10. The method according to claim 9, wherein the surfactant is a cationic surfactant, an anionic surfactant, a non-ionic surfactant or any combinations thereof.

11. The method according to claim 9, wherein the silane source comprises tetraethoxysilane (TEOS), tetramethoxysilane (TMOS), sodium silicate or a mixture thereof.

12. The method according to claim 9, wherein the surface modifying agent is selected from 2-[methoxy(polyethyleneoxy)propyl]-trimethoxysilane(PEG-trimethoxysilane), 3-aminopropyltrimethoxysilane (APTMS), propyl triethoxysilane, butyl trimethoxysilane, octyltrimethoxysilane, diphenyl diethoxysilane, n-octyltriethoxysilane, mercapto propyl trimethoxysilane, chloro methyl trimethoxysilane, isobutyl triethoxysilane, 3-aminopropyl triethoxysilane, ethyl trimethoxy styrene silane, methyl triethoxysilane, phenyltriethoxysilane (PTEOS), phenyltrimethoxysilane (PTMOS), methyltrimethoxysilane (MTMOS), ethyltriacetoxysilane (ETAS), N-(trimethoxysilylpropyl) ethylenediaminetriacetic acid (EDTAS), (3-trihydroxysilyl) propyl methylphosphonate (THPMP), methyltriacetoxysilane(MTAS), N-[3-(trimethoxysilyl)propyl]ethylenediamine, trimethoxysilylpropyl modified (polyethlenimine), (3-mercatopropyl)trimethoxysilane (MPTMS), N-[3-(trimethoxysilyl)propyl]-N,N,N-trimethylammonium chloride, zwitterionic silane and a mixture thereof.

13. The method according to claim 9, wherein the silane source is a mixture of TEOS and APTMS, a mixture of THPMP, APTMS and TEOS, a mixture of EDTAS, APTMS and TEOS or a mixture of PTEOS and TEOS or a mixture of PTMOS and TEOS.

14. The method according to claim 9, wherein the mesoporous silica nanoparticle (MSN) further comprises a bioactive ingredient selected from a small molecule drug, a protein such as an enzyme and a protein drug, an antibody, a vaccine, an antibiotic or a nucleotide drug.

15. A mesoporous silica nanoparticle, which is prepared by the method of claim 9.

16. A method of inhibiting cellular metastasis in a subject comprising administering a mesoporous silica nanoparticle to the subject through systemic or local administration.

17. The method according to claim 16, wherein the mesoporous silica nanoparticle has a particle size of about 200 nm or less, preferably about 50 nm or less.

18. The method according to claim 16, wherein the mesoporous silica nanoparticle has PEG modification on the surface.

19. The method according to claim 16, wherein the mesoporous silica nanoparticle has a BET surface area of about 1000 $m^2/g$ or less, preferably about 500 $m^2/g$.

20. The method according to claim 16, wherein the cellular metastasis is carcinoma cell metastasis, preferably breast carcinoma.

21. The mesoporous silica nanoparticle according to claim 1, wherein the surface of the nanoparticle comprises further modification derived from at least one surface modifying agent selected from N-[3-(trimethoxysilyl)propyl]-N,N,N-trimethylammonium chloride (TA), N-[3(Trimethoxysilyl)propyl]ethylenediamine (EDPT), $N^1$-(3-Trimethoxysilylpropyl)diethylenetriamine, 3-aminopropyltrimethoxysilane (APTMS), propyl triethoxysilane, butyl trimethoxysilane, octyltrimethoxysilane, diphenyl diethoxysilane, n-octyltriethoxysilane, mercapto propyl trimethoxysilane, chloro methyl trimethoxysilane, isobutyl triethoxysilane, 3-aminopropyl triethoxysilane, ethyl trimethoxy styrene silane, methyl triethoxysilane, phenyltriethoxysilane (PTEOS), phenyltrimethoxysilane (PTMOS), methyltrimethoxysilane (MTMOS), ethyltriacetoxysilane (ETAS), N-(trimethoxysilylpropyl) ethylenediaminetriacetic acid (EDTAS), (3-trihydroxysilyl) propyl methylphosphonate (THPMP), methyltriacetoxysilane(MTAS) or (3-mercatopropyl) trimethoxysilane (MPTMS).

22. The mesoporous silica nanoparticle according to claim 8, wherein the protein is an enzyme or a protein drug.

23. The mesoporous silica nanoparticle according to claim 1, wherein the surface of the nanoparticle comprises modification derived from at least one surface modifying agent selected from polyethylenimine (PEI), N-[3-(trimethoxysilyl)propyl]-N,N,N-trimethylammonium chloride (TA), N-[3-(Trimethoxysilyl)propyl]ethylenedamine (EDPT), $N^1$-(3-Trimethoxysilylpropyl)diethylenetriamine, 3-aminopropyltrimethoxysilane (APTMS), or 3-aminopropyl triethoxysilane.

* * * * *